United States Patent
Chen et al.

(10) Patent No.: US 11,370,739 B2
(45) Date of Patent: Jun. 28, 2022

(54) SACUBITRIL INTERMEDIATE AND PREPARATION METHOD THEREOF

(71) Applicant: NORTH & SOUTH BROTHER PHARMACY INVESTMENT COMPANY LIMITED, Wanchai (HK)

(72) Inventors: Lei Chen, Dongguan (CN); Guodong Sun, Dongguan (CN); Xiaodong Han, Dongguan (CN); Shun Li, Dongguan (CN); Jiebin Zeng, Dongguan (CN); Zhongqing Wang, Dongguan (CN); Zhonghua Luo, Dongguan (CN)

(73) Assignee: Sunshine Lake Pharma Co., Ltd., Guangdong (CN)

( * ) Notice: Subject to any disclaimer, the term of this patent is extended or adjusted under 35 U.S.C. 154(b) by 417 days.

(21) Appl. No.: 16/679,154

(22) Filed: Nov. 9, 2019

(65) Prior Publication Data

US 2020/0079721 A1    Mar. 12, 2020

Related U.S. Application Data

(60) Division of application No. 16/112,761, filed on Aug. 26, 2018, now Pat. No. 10,479,753, which is a continuation-in-part of application No. PCT/CN2017/075097, filed on Feb. 28, 2017.

(30) Foreign Application Priority Data

Feb. 29, 2016 (CN) .......................... 201610111396.6

(51) Int. Cl.
| | | |
|---|---|---|
| C07C 59/205 | (2006.01) |
| C07C 231/02 | (2006.01) |
| C07C 233/47 | (2006.01) |
| C07C 51/09 | (2006.01) |
| C12P 13/00 | (2006.01) |
| C07C 235/78 | (2006.01) |
| C07C 59/84 | (2006.01) |
| C07C 69/738 | (2006.01) |
| C07C 49/245 | (2006.01) |
| C07C 49/255 | (2006.01) |
| C07D 498/04 | (2006.01) |
| C07C 45/65 | (2006.01) |
| C07C 49/35 | (2006.01) |
| C07C 67/317 | (2006.01) |
| C07C 69/716 | (2006.01) |
| C07C 231/12 | (2006.01) |
| C07C 233/11 | (2006.01) |
| C07F 7/18 | (2006.01) |

(52) U.S. Cl.
CPC ............ *C07C 59/205* (2013.01); *C07C 45/65* (2013.01); *C07C 49/245* (2013.01); *C07C 49/255* (2013.01); *C07C 49/35* (2013.01); *C07C 51/09* (2013.01); *C07C 59/84* (2013.01); *C07C 67/317* (2013.01); *C07C 69/716* (2013.01); *C07C 69/738* (2013.01); *C07C 231/02* (2013.01); *C07C 231/12* (2013.01); *C07C 233/11* (2013.01); *C07C 233/47* (2013.01); *C07C 235/78* (2013.01); *C07D 498/04* (2013.01); *C07F 7/1892* (2013.01); *C12P 13/00* (2013.01)

(58) Field of Classification Search
None
See application file for complete search history.

(56) References Cited

U.S. PATENT DOCUMENTS

| 4,604,383 A | 8/1986 | Biziere et al. |
|---|---|---|
| 9,242,927 B2 | 1/2016 | Zhu |

FOREIGN PATENT DOCUMENTS

| CN | 104557600 A | 4/2015 |
|---|---|---|
| CN | 104557600 | 8/2015 |
| CN | 104860894 | 8/2015 |
| CN | 104860894 A | 8/2015 |
| CN | 105924355 | 9/2016 |
| CN | 105924355 A | 9/2016 |
| CN | 106977415 | 7/2017 |
| CN | 106977415 A | 7/2017 |
| CN | 107602399 | 1/2018 |
| CN | 107602399 A | 1/2018 |
| WO | 2008083967 A2 | 7/2008 |
| WO | 2017098430 A1 | 6/2017 |

OTHER PUBLICATIONS

Norman Aubry et al., Tetrahedron Letters, 1990, 31(44), 6311-6312.
Laurence E. Burgess et al., J. Org. Chem. 1992, 57, 1656-1662.
Mo Xian et al., J. Org. Chem. 2007, 72, 7560-7566.
ISR of PCT/CN2017/075097.
Written Opinion of the ISA of PCT/CN2017/075097.
Extended European Search Report for European application based on PCT/CN2017/075097.
Nathalie E. Wurz et al., Chemistry—A European Journal, vol. 18, No. 51, (2012), pp. 16297-16301.
Jakob Karaffa et al., Journal of Organic Chemistry, vol. 71, No. 21, (2006), pp. 8219-8226.
Philip Deshong et al., Journal of the American Chemical Society, vol. 110, No. 8, (1988), pp. 2575-2585.
Kateryna Fesko et al., Journal of Molecular Catalysis. B, Enzymatic, vol. 96, (2013), pp. 103-110.

*Primary Examiner* — Clinton A Brooks
(74) *Attorney, Agent, or Firm* — Law Kam Wah

(57) ABSTRACT

The present invention relates to a sacubitril intermediate and a preparation method thereof. The sacubitril intermediate disclosed herein can be prepared by a deprotection reaction of a compound. In addition, the intermediate can be used as a raw material to synthesize sacubitril.

16 Claims, No Drawings

SACUBITRIL INTERMEDIATE AND PREPARATION METHOD THEREOF

CROSS-REFERENCE TO RELATED APPLICATIONS

This is a divisional application of the U.S. patent application Ser. No. 16/112,761, filed Aug. 26, 2018, which is a continuation-in-part application of the International Patent Application No. PCT/CN2017/075097, filed Feb. 28, 2017, which claims priority to Chinese Patent Application No. 201610111396.6, filed Feb. 29, 2016, all of which are incorporated herein by reference in their entirety.

FIELD OF THE INVENTION

The present invention relates to the medical and chemical industry field, more specifically to a sacubitril intermediate and a preparation method thereof.

BACKGROUND OF THE INVENTION

Sacubitril, the chemical name is 4-(((2S,4R)-1-([1,1'-biphenyl]-4-yl)-5-ethoxy-4-methyl-5-oxopentan-2-yl)amino)-4-oxobutanoic acid, the structure is as following:

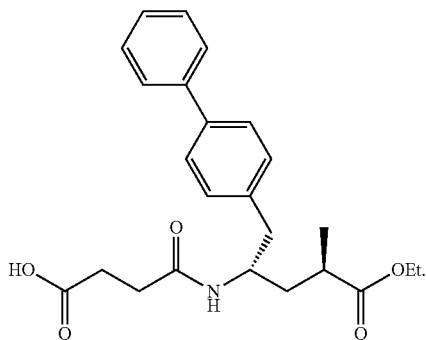 [SMILES: CCOC(=O)[C@H](C)C[C@@H](Cc1ccc(-c2ccccc2)cc1)NC(=O)CCC(=O)O]

U.S. FDA approved the anti-heart failure (anti-HF) drug Entresto (known as LCZ696) on July, 2015, which is a complex of the angiotensin II inhibitor valsartan and the enkephalinase inhibitor sacubitril. Valsartan can improve vasodilation and stimulate the body to excrete sodium and water, and sacubitril can block the mechanism of action of two peptides that threaten to lower blood pressure, thus LCZ696 is known as a dual inhibitor of angiotensin II receptor and enkephalinase, its clinical manifestation is a unique mode of action, which is superior to the standard drugs with respect to antihypertensive effect and the efficacy of reducing heart failure.

Some methods of preparing sacubitril are disclosed in the prior art, such as:

Patent application WO2008031567A1 disclosed a method of preparing biphenyl butyric acid substituted on 4 position amino or derivative thereof by using biphenyl propanol substituted on 2 position amino as starting materials, which was oxidized to aldehyde, and the aldehyde was suffered from Witting reaction to give biphenyl butenoic acid substituted on 4 position amino or derivative thereof, and the biphenyl butenoic acid substituted on 4 position amino or derivative thereof was suffered from a reduction reaction under $H_2$ in the presence of transition metal of group 7, 8 and 9 in the chemical periodic table as catalyst and a chiral ligand, and then chiral separation to give biphenyl butyric acid substituted on 4 position amino or derivative thereof. The product can be converted to sacubitril. The process of the method is depicted as follows:

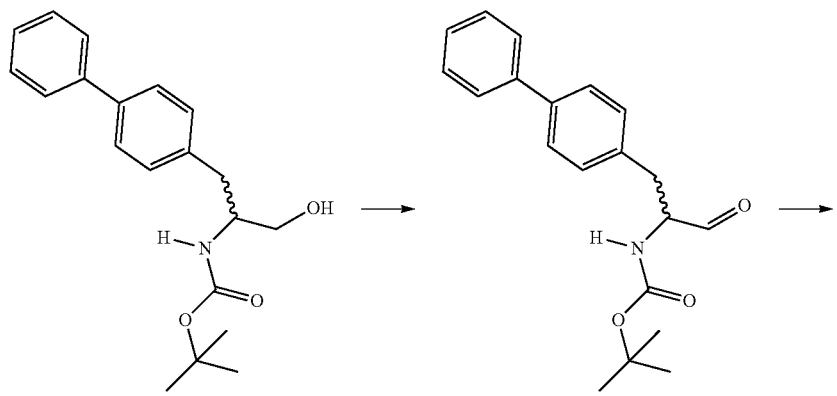

-continued
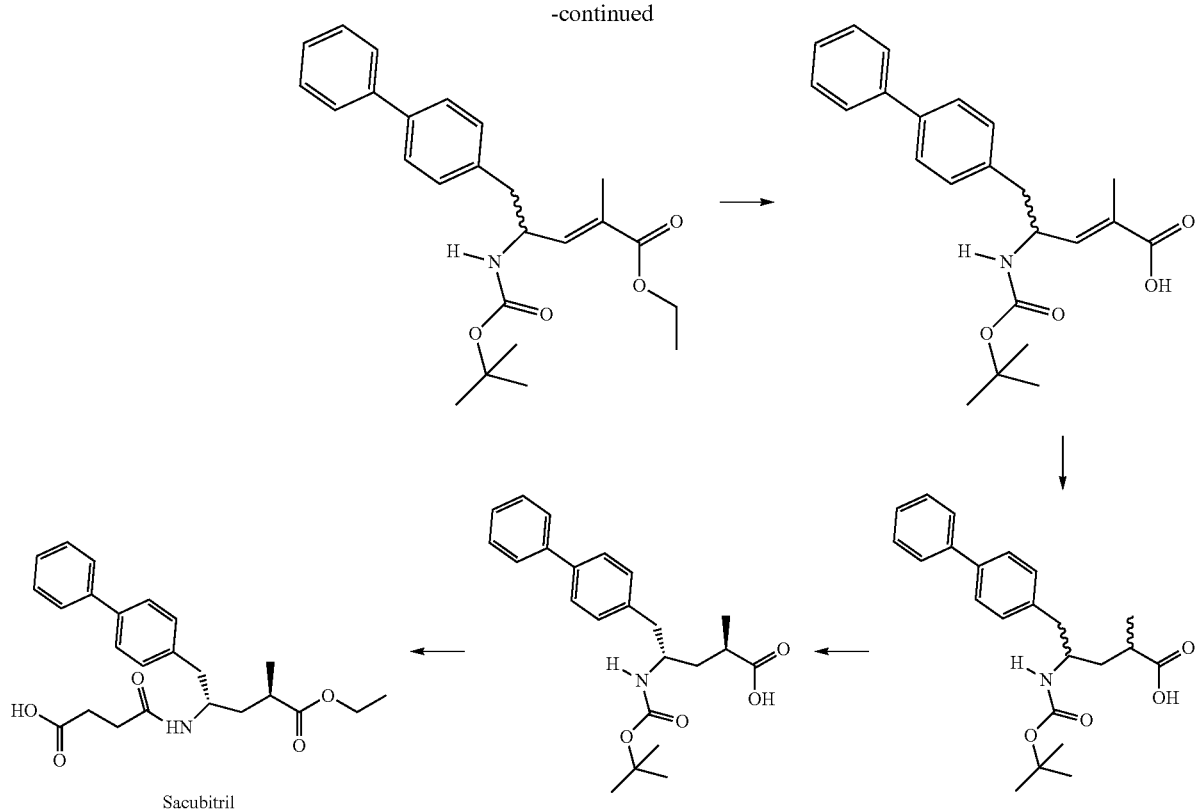
Sacubitril
Patent application WO2008083967A2 disclosed a method of preparing sacubitril using 2-carbonylproline as a starting material, which was suffered from carboxy activation, biphenyl substitution, carbonyl reduction, chiral methylation, ring opening reaction and amide condensation and so on to give sacubitril. The reaction is depicted as follows:

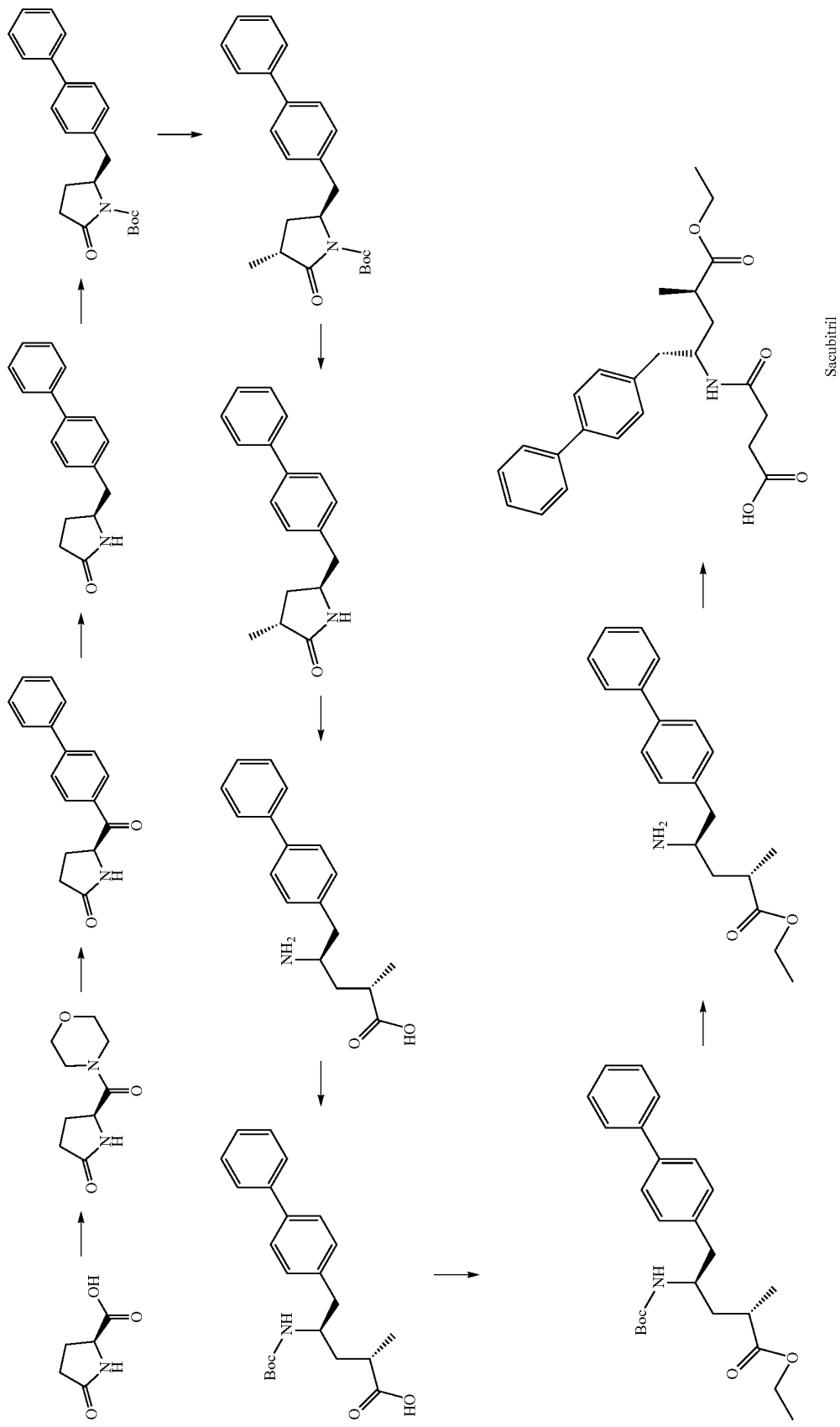

The synthetic routes disclosed in patent applications WO 2008031567A1 and WO 2008083967A2 have some differences in the use of the raw materials, forming method of chirality and order of unit reactions, however, there are disadvantages such as difficulty in obtaining chiral raw materials, many reaction steps, expensive chiral catalytic reduction catalysts, poor stereoselectivity, and repeated use of carboxy or amino protection and deprotection, it is difficult to achieve industrialization smoothly.

Chiral induction agent (S)-1-(α-aminobenzyl)-2-naphthol (S-betti Base) with 2R-methyl-4-oxo-butanoic acid were suffered from cyclization, addition, debenzylation, ring opening, esterification and amidation and so on to give sacubitril disclosed in CN104557600A. The process is depicted as follows:

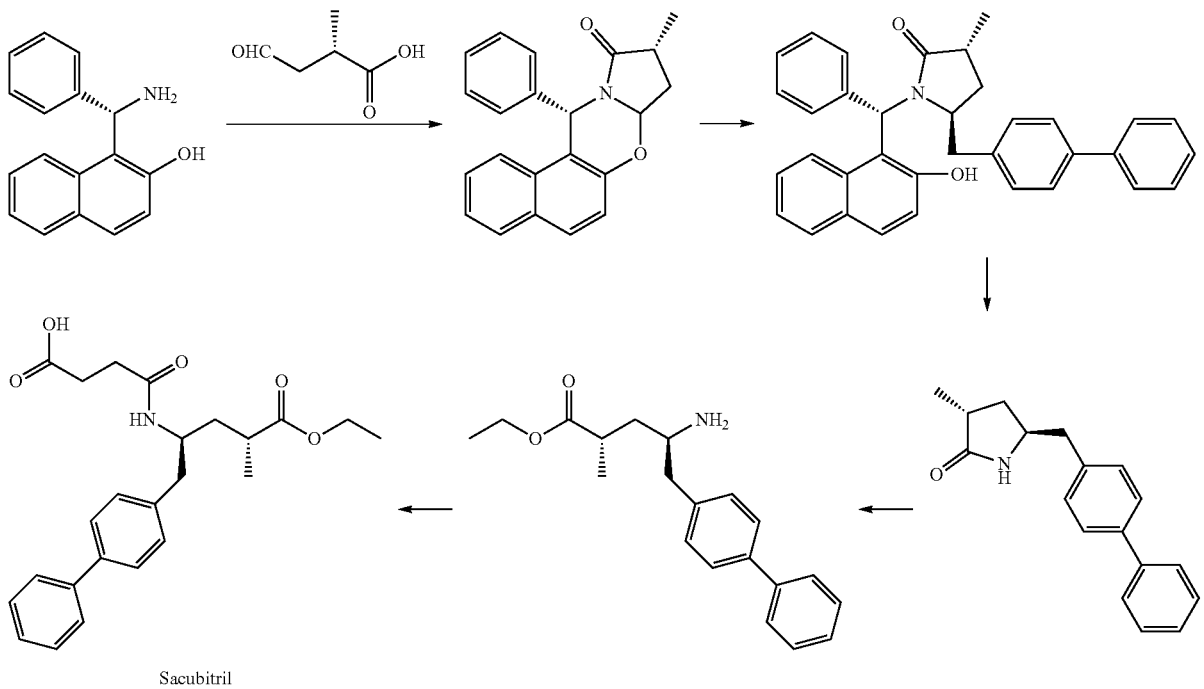

Sacubitril

The process of preparing sacubitril has disadvantages of expensive and not readily available S-betti Base and chiral starting materials, preparation of Grignard reagent before addition reaction, strict reaction conditions, uncontrollable, and more cumbersome synthetic route.

SUMMARY OF THE INVENTION

In a first aspect, provided herein are an intermediate for preparing sacubitril shown as a compound of Formula (V), and a preparation method of the compound of Formula (V);

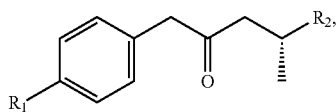

(V)

wherein $R_1$ may be phenyl, methoxy, hydroxy, chloro, bromo, iodo, mesylate (—OMs), triflate (—OTf) or 4-methylbenzenesulfonate (—OTs);

$R_2$ may be

—C(=O)—O—$R_3$, —C(=O)—N(H)—$R_3$ or

—CH$_2$—O—$R_4$;

$R_3$ may be H, —($C_1$-$C_4$)alkyl or —($C_1$-$C_4$)alkyl-aryl. Wherein —($C_1$-$C_4$)alkyl in some embodiments may be methyl, ethyl, n-propyl, i-propyl, n-butyl, t-butyl. Wherein —($C_1$-$C_4$)alkyl-aryl in some embodiments may be benzyl or optionally substituted benzyl.

$R_4$ may be H, —($C_1$-$C_4$)alkyl, —($C_3$-$C_6$)heterocyclyl, —($C_1$-$C_4$)alkyl-aryl, trimethylsilyl, triethylsilyl or t-butyldimethylsilyl. Wherein —($C_1$-$C_4$)alkyl in some embodiments may be methyl, ethyl, n-propyl, i-propyl, n-butyl, t-butyl. Wherein —($C_1$-$C_4$)alkyl-aryl in some embodiments may be benzyl or optionally substituted benzyl.

In a second aspect, provided herein are two methods of preparing sacubitril from a compound of Formula (V), the two methods have advantages of easily obtained raw materials, simple preparation process, low cost and friendly environment, and so on, which are suitable for industrial production.

In a third aspect, provided herein is a compound of Formula (V),

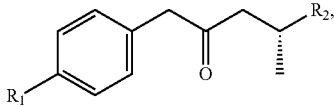

wherein:

R₁ is phenyl, methoxy, hydroxy, chloro, bromo, iodo, mesylate, triflate or 4-methylbenzenesulfonate;

R₂ is

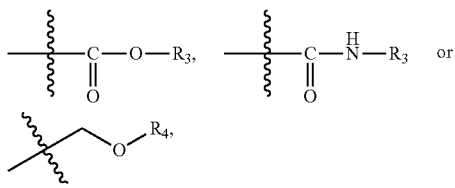

and when R₁ is phenyl, R₂ is not

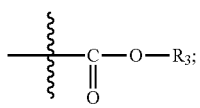

R₃ is H, —(C₁-C₄)alkyl or —(C₁-C₄)alkyl-aryl; and R₄ is H, —(C₁-C₄)alkyl, —(C₃-C₆)heterocyclyl, —(C₁-C₄)alkyl-aryl, trimethylsilyl, triethylsilyl or t-butyldimethylsilyl.

In some embodiments, R₁ is phenyl. In certain embodiments, R₃ is H, methyl, ethyl, n-propyl, i-propyl, n-butyl, t-butyl, benzyl or optionally substituted benzyl. In some embodiments, R₄ is H, methyl, ethyl, n-propyl, i-propyl, n-butyl, t-butyl, trimethylsilyl, triethylsilyl, t-butyldimethylsilyl, triphenylmethyl, tetrahydrofuryl, benzyl or optionally substituted benzyl. In certain embodiments, R₂ is —COOH, —COOCH₃, —COOCH₂CH₃, —COOCH(CH₃)₂, —COOC(CH₃)₃, —COOCH₂Ph, —CH₂OH, —CH₂OCH₃, —CH₂OCH₂CH₃, —CH₂OCH(CH₃)₂, —CH₂OC(CH₃)₃, —CH₂OCH₂Ph, —CH₂OC(Ph)₃, —CH₂OSi(CH₃)₃, —CH₂OSi(CH₂CH₃)₃, —CH₂OSi(CH₃)₂C(CH₃)₃, —CONH₂, —CONHCH₃, —CONHCH₂CH₃, —CONHCH(CH₃)₂, —CONHC(CH₃)₃, —CONHCH₂Ph or

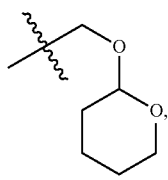 [SMILES: *COC1CCCCO1]

and when R₁ is phenyl, R₂ is —CH₂OH, —CH₂OCH₃, —CH₂OCH₂CH₃, —CH₂OCH(CH₃)₂, —CH₂OC(CH₃)₃, —CH₂OCH₂Ph, —CH₂OC(Ph)₃, —CH₂OSi(CH₃)₃, —CH₂OSi(CH₂CH₃)₃, —CH₂OSi(CH₃)₂C(CH₃)₃, —CONH₂, —CONHCH₃, —CONHCH₂CH₃, —CONHCH(CH₃)₂, —CONHC(CH₃)₃, —CONHCH₂Ph or

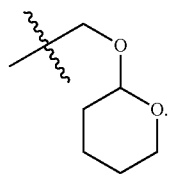 [SMILES: *COC1CCCCO1]

In a fourth aspect, provided herein is a method of preparing a compound of Formula (V):

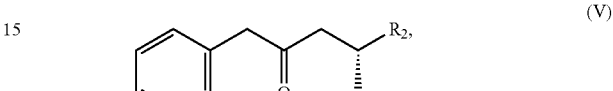

wherein the compound of Formula (V) is prepared by a deprotection reaction of a compound of Formula (IV):

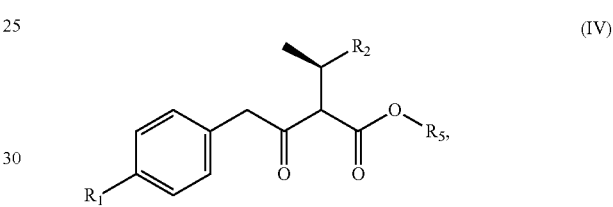

in the presence of a base or an acid, wherein:

R₁ is phenyl, methoxy, hydroxy, chloro, bromo, iodo, mesylate, triflate or 4-methylbenzenesulfonate;

R₂ is

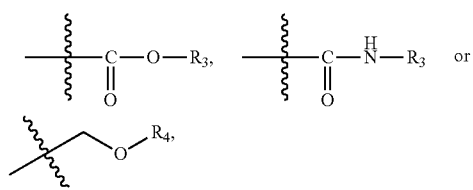

and when R₁ is phenyl, R₂ is not

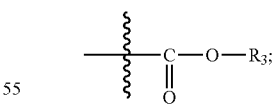

R₃ is H, —(C₁-C₄)alkyl or —(C₁-C₄)alkyl-aryl;

R₄ is H, —(C₁-C₄)alkyl, —(C₃-C₆)heterocyclyl, —(C₁-C₄)alkyl-aryl, trimethylsilyl, triethylsilyl or t-butyldimethylsilyl; and R₅ is H, —(C₁-C₄)alkyl or —(C₁-C₄)alkyl-aryl.

In some embodiments, the compound of Formula (IV) is prepared by a substitution reaction of a compound of Formula (II) with a compound of Formula (III) in the presence of a base;

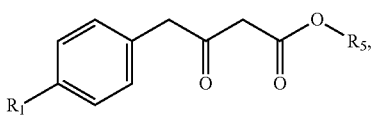 (II)

 (III)

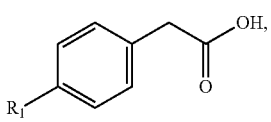 (IV)

In certain embodiments, the compound of Formula (II) is prepared by a condensation reaction of a compound of Formula (I);

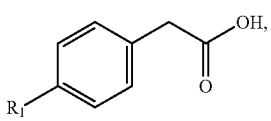 (I)

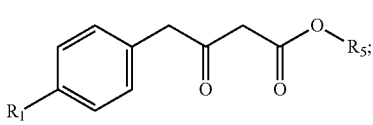 (II)

wherein $R_1$ is as defined above; and
$R_5$ is H, —($C_1$-$C_4$)alkyl or —($C_1$-$C_4$)alkyl-aryl.

In some embodiments, the compound of the Formula (IV) is prepared by a process comprising the following steps:

a) preparing a compound of Formula (II) by a condensation reaction of a compound of Formula (I) in the presence of a base,

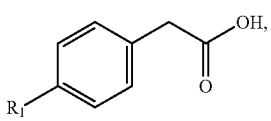 (I)

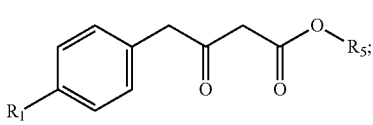 (II)

and b) preparing a compound of Formula (IV) by a substitution reaction of the compound of Formula (II) with a compound of Formula (III) in the presence of a strong base;

 (III)

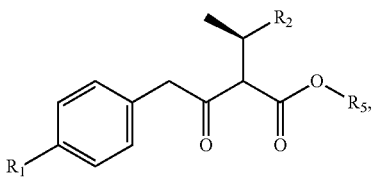 (IV)

wherein $R_1$ is phenyl;
$R_2$ is

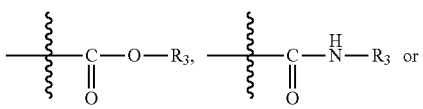

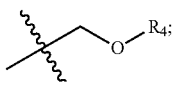

$R_3$ is H, methyl, ethyl, n-propyl, i-propyl, n-butyl, t-butyl or benzyl;

$R_4$ is H, methyl, ethyl, n-propyl, i-propyl, n-butyl, t-butyl, benzyl, trimethylsilyl, triethylsilyl, t-butyldimethylsilyl, triphenylmethyl, tetrahydrofuryl;

$R_5$ is H, methyl, ethyl, n-propyl, i-propyl, n-butyl or benzyl; and $R_6$ is triflate, mesylate or 4-methylbenzenesulfonate.

In certain embodiments, the compound of Formula (II) is prepared by a condensation reaction of the compound of Formula (I) with N,N'-carbonyldiimidazole and a compound of Formula (VIII):

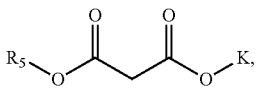 (VIII)

in the presence of magnesium chloride and triethylamine, wherein $R_5$ is H, —($C_1$-$C_4$)alkyl or —($C_1$-$C_4$)alkyl-aryl.

In some embodiments, the compound of Formula (II) is prepared by a condensation reaction of the compound of Formula (I) with Meldrum's acid, 4-dimethylaminopyridine, $R_5$OH and pivaloyl chloride in the presence of N,N-diisopropylethylamine, $R_5$ is H, —($C_1$-$C_4$)alkyl or —($C_1$-$C_4$) alkyl-aryl.

In a fifth aspect, provided herein is a method of preparing sacubitril,

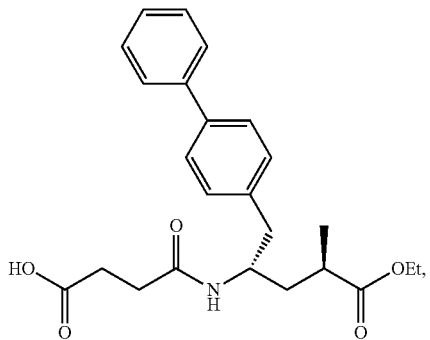 [SMILES: CCOC(=O)[C@H](C)C[C@@H](Cc1ccc(-c2ccccc2)cc1)NC(=O)CCC(=O)O]

comprising the following steps:
a) preparing a compound of Formula (VI) by an enzymic catalytic reaction of a compound of Formula (V) in the presence of ω-transaminase and phosphopyridoxal, (V)

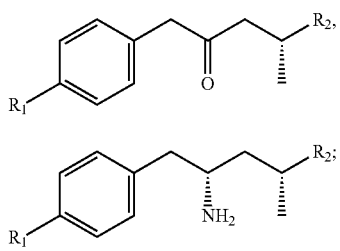

(VI)

b) optionally, preparing a compound of Formula (VII) from the compound of Formula (VI):

(VII)

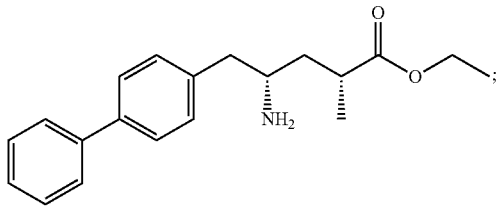

and c) preparing sacubitril from the compound of Formula (VII), wherein:
$R_1$ is phenyl, methoxy, hydroxy, chloro, bromo, iodo, mesylate, triflate or 4-methylbenzenesulfonate;
$R_2$ is

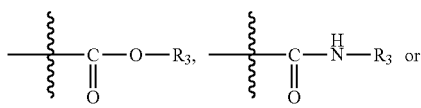

-continued

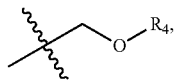

$R_3$ is H, —($C_1$-$C_4$)alkyl or —($C_1$-$C_4$)alkyl-aryl; and
$R_4$ is H, —($C_1$-$C_4$)alkyl, —($C_3$-$C_6$)heterocyclyl, —($C_1$-$C_4$)alkyl-aryl, trimethylsilyl, triethylsilyl or t-butyldimethylsilyl.

In certain embodiments, $R_1$ is phenyl; $R_2$ is

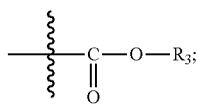

and $R_3$ is methyl, ethyl, propyl, i-propyl, n-butyl, t-butyl, benzyl or optionally substituted benzyl.

In some embodiments, the method of preparing sacubitril comprises the following steps:
a) preparing a compound of Formula (VII) by an enzymic catalytic reaction of a compound of Formula (V):

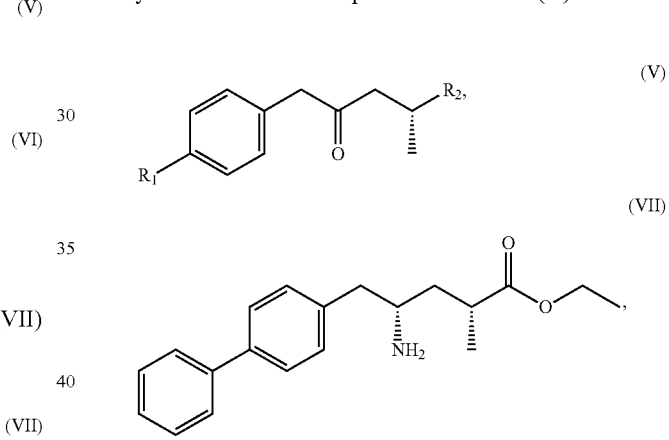

in the presence of ω-transaminase and phosphopyridoxal; and b) preparing sacubitril by an amide condensation reaction of the compound of Formula (VII) with succinic anhydride, wherein $R_1$ is phenyl, and $R_2$ is

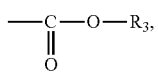

and $R_3$ is ethyl.

In certain embodiments, the compound of Formula (VII) is prepared by a hydrolysis reaction of the compound of Formula (VI) and then an esterification reaction of the hydrolysis product with ethanol.

In some embodiments, the compound of the Formula (VII) is prepared by a process comprising the following steps:
a) preparing a compound of Formula (X) by a reaction of a compound of Formula (V) with a compound of Formula (IX),

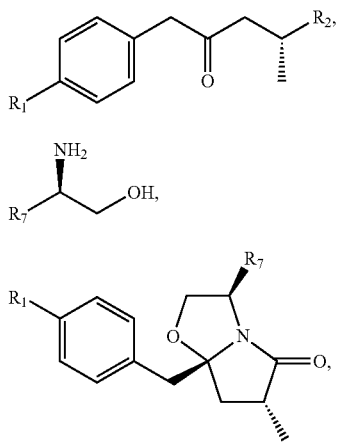

(V)

(IX)

b) preparing a compound of Formula (XI) from the compound of Formula (X),

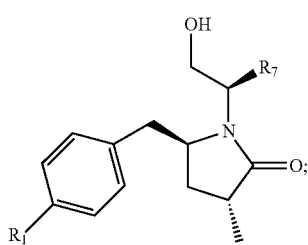

(XI)

c) preparing a compound of Formula (XII) from the compound of Formula (XI),

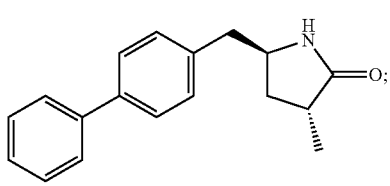

(XII)

d) preparing a compound of Formula (VII) from the compound of Formula (XII),

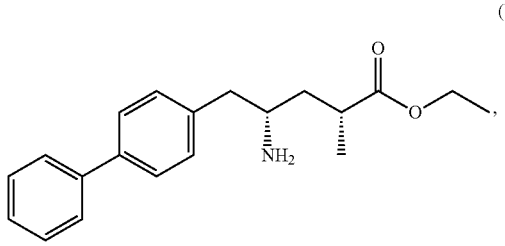

(VII)

wherein:
R$_1$ is phenyl, methoxy, hydroxy, chloro, bromo, iodo, mesylate, triflate or 4-methylbenzenesulfonate;

R$_2$ is

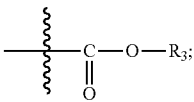

R$_3$ is H, —(C$_1$-C$_4$)alkyl or —(C$_1$-C$_4$)alkyl-aryl; and
R$_7$ is phenyl, —(C$_1$-C$_4$)alkyl or —(C$_1$-C$_4$)alkyl-aryl.

In certain embodiments, the compound of Formula (IX) in step a) is D-phenylglycinol.

In some embodiments, the compound of Formula (XI) is prepared from the compound of Formula (X) in the presence of titanium tetrachloride and triethyl silicane in step b).

In certain embodiments, the compound of Formula (XII) is prepared from the compound of Formula (XI) in the presence of palladium-carbon in step c).

In some embodiments, the compound of Formula (VII) is prepared from the compound of Formula (XII) in ethanol in the presence of an acid in step d).

In certain embodiments, the compound of the Formula (VII) is prepared by a process comprising the following steps:

a) preparing a compound of Formula (XIII) by a reaction of (R)-5-([1,1'-biphenyl]-4-yl)-2-methyl-4-oxopentanoic acid with D-phenylglycinol, (XIII)

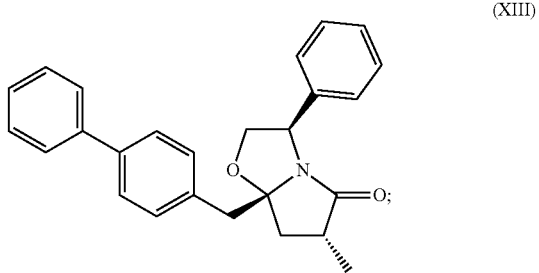 [SMILES: C[C@@H]1C[C@]2(Cc3ccc(-c4ccccc4)cc3)OC[C@@H](c3ccccc3)N2C1=O]

b) preparing a compound of Formula (XIV) from the compound of Formula (XIII) in the presence of titanium tetrachloride and triethyl silicane, (XIV)

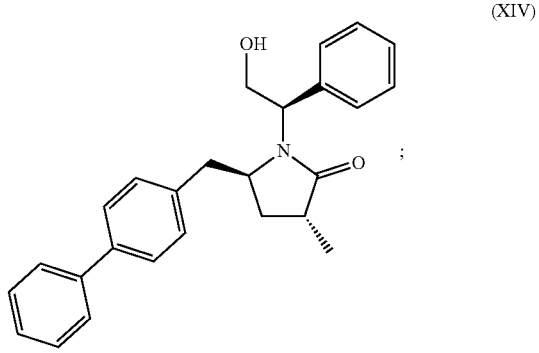 [SMILES: C[C@@H]1C[C@@H](Cc2ccc(-c3ccccc3)cc2)N([C@@H](CO)c2ccccc2)C1=O ; ";"]

c) preparing a compound of Formula (XII) from the compound of Formula (XIV) in the presence of palladium-carbon,

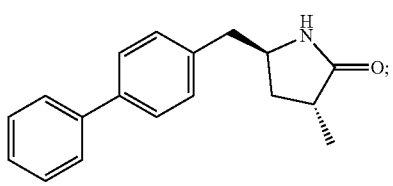

and d) preparing a compound of Formula (VII) by a ring opening reaction of the compound of Formula (XII):

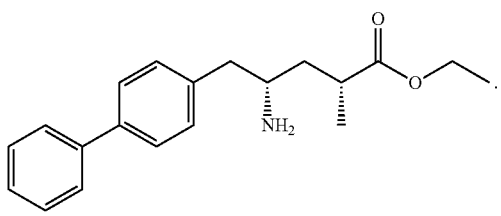

Definition of Terms

The invention is intended to cover all alternatives, modifications, and equivalents which are included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated.

For purposes of this invention, the chemical elements are identified in accordance with the Periodic Table of the Elements, CAS version, and the Handbook of Chemistry and Physics, 75th Ed. 1994. The term "comprising" or "comprise" is meant to be open ended, including the indicated component but not excluding other elements.

At various places in the present specification, substituents of compounds disclosed herein are disclosed in groups or in ranges. It is specifically intended that the invention include each and every individual subcombination of the members of such groups and ranges. For example, the term "—$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" refers to a saturated linear or branched-chain monovalent hydrocarbon group of 1-20 carbon atoms, wherein the alkyl group is optionally substituted with one or more substituents described herein.

The term "heterocyclyl" refers to a saturated or partially unsaturated, monocyclic, bicyclic or tricyclic ring containing 3 to 12 ring atoms, in which at least one ring member is selected from nitrogen, sulfur and oxygen. Unless otherwise specified, the heterocyclyl group may be carbon or nitrogen linked, and a —$CH_2$-group can be optionally replaced by a —C(O)— group. In which, the sulfur can be optionally oxygenized to S-oxide and the nitrogen can be optionally oxygenized to N-oxide. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, indolinyl, 1,2,3,4-tetrahydroisoquinolyl, 1,3-benzodioxolyl, 2-oxa-5-azabicyclo[2.2.1]hept-5-yl, and the like. Some non-limiting examples of heterocyclyl wherein —$CH_2$— group is replaced by —C(O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of heterocyclyl wherein the ring sulfur atom is oxidized is sulfolanyl, 1,1-dioxo-thiomorpholinyl. The heterocyclyl group may be optionally substituted with one or more substituents disclosed herein.

In some embodiments, heterocyclyl may be 6 membered heterocyclyl, which refers to a saturated or partially unsaturated monocyclic ring containing 6 ring atoms, of which at least one ring atom is selected from nitrogen, sulfur and oxygen. Unless otherwise specified, the heterocyclyl group containing 6 ring atoms may be carbon or nitrogen linked, and a —$CH_2$-group can be optionally replaced by a —C(O)— group. In which, the sulfur can be optionally oxygenized to S-oxide and the nitrogen can be optionally oxygenized to N-oxide. Examples of the heterocyclyl group containing 6 ring atoms include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl and thioxanyl. Some non-limiting examples of heterocyclyl wherein —$CH_2$— group is replaced by —C(O)— moiety include 2-piperidinonyl, 3,5-dioxopiperidinyl and pyrimidinedionyl. Some non-limiting examples of heterocyclyl wherein the ring sulfur atom is oxidized is 1,1-dioxo-thiomorpholinyl. The heterocyclyl group containing 6 ring atoms may be optionally substituted with one or more substituents disclosed herein.

The term "unsaturated" refers to a moiety having one or more units of unsaturation.

The term "heteroatom" refers to one or more of oxygen, sulfur, nitrogen, phosphorus and silicon, including any oxidized form of nitrogen, sulfur, or phosphorus; primary, secondary, tertiary amine and the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "aryl refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" and "aromatic ring" can be used interchangeably herein. Examples of aryl ring may include phenyl, naphthyl and anthracene. The aryl group may be optionally and independently substituted with one or more substituents disclosed herein.

Mesylate (—OMs) disclosed herein is

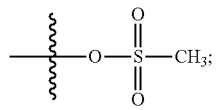 [SMILES: *OS(C)(=O)=O]

triflate (—OTf) disclosed herein is

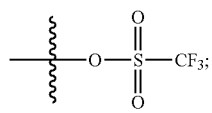 [SMILES: *OS(=O)(=O)C(F)(F)F]

4-methylbenzenesulfonate (—OTs) is

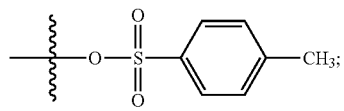 [SMILES: *OS(=O)(=O)c1ccc(C)cc1]

and Ph is phenyl.

DETAILED DESCRIPTION OF THE INVENTION

In first aspect, provided herein are an intermediate for preparing sacubitril shown as a compound of Formula (V); and also a preparation method of the compound of Formula (V).

Provided herein is an intermediate for preparing sacubitril, shown as a compound of Formula (V):

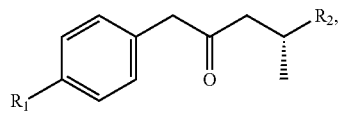

(V)

wherein $R_1$ may be phenyl, methoxy, hydroxy, chloro, bromo, iodo, mesylate (—OMs), triflate (—OTf) or 4-methylbenzenesulfonate (—OTs) and in some embodiments, $R_1$ is phenyl;

$R_2$ may be

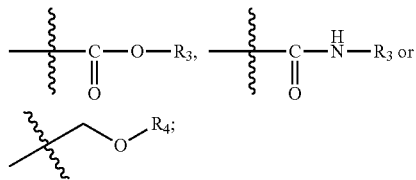

$R_3$ may be H, —($C_1$-$C_4$)alkyl or —($C_1$-$C_4$)alkyl-aryl; wherein —($C_1$-$C_4$)alkyl in some embodiments may be methyl, ethyl, n-propyl, i-propyl, n-butyl, t-butyl; wherein —($C_1$-$C_4$)alkyl-aryl in some embodiments may be benzyl or optionally substituted benzyl;

$R_4$ may be H, —($C_1$-$C_4$)alkyl, —($C_3$-$C_6$)heterocyclyl, —($C_1$-$C_4$)alkyl-aryl, trimethylsilyl, triethylsilyl or t-butyldimethylsilyl; wherein —($C_1$-$C_4$)alkyl in some embodiments may be methyl, ethyl, n-propyl, i-propyl, n-butyl, t-butyl; wherein —($C_1$-$C_4$)alkyl-aryl in some embodiments may be benzyl or optionally substituted benzyl.

In some embodiments, when $R_1$ of any formulae disclosed herein is phenyl, $R_2$ is not

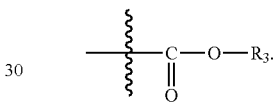

In some embodiments, the compound of Formula (V) disclosed herein, wherein $R_2$ is —COOH, —COOCH$_3$, —COOCH$_2$CH$_3$, —COOCH(CH$_3$)$_2$, —COOC(CH$_3$)$_3$, —COOCH$_2$Ph, —CH$_2$OH, —CH$_2$OCH$_3$, —CH$_2$OCH$_2$CH$_3$, —CH$_2$OCH(CH$_3$)$_2$, —CH$_2$OC(CH$_3$)$_3$, —CH$_2$OCH$_2$Ph, —CH$_2$OC(Ph)$_3$, —CH$_2$OSi(CH$_3$)$_3$, —CH$_2$OSi(CH$_2$CH$_3$)$_3$, —CH$_2$OSi(CH$_3$)$_2$C(CH$_3$)$_3$, —CONH$_2$, —CONHCH$_3$, —CONHCH$_2$CH$_3$, —CONHCH(CH$_3$)$_2$, —CONHC(CH$_3$)$_3$, —CONHCH$_2$Ph or

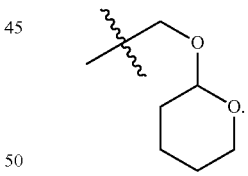

In some embodiments, the compound of Formula (V) may be one of the following structures:

| No. | Compound of Formula (V) |
|---|---|
| (1) |  |

-continued

| No. | Compound of Formula (V) |
|---|---|
| (2) | methyl (2R)-4-(biphenyl-4-yl)-2-methyl-3-oxobutanoate derivative with OCH₃ ester |
| (3) | ethyl ester analog (OEt) |
| (4) | isopropyl ester analog |
| (5) | tert-butyl ester analog |
| (6) | benzyl ester analog (OCH₂Ph) |
| (7) | 5-(biphenyl-4-yl)-4-oxo-2-methylpentan-1-ol |
| (8) | methyl ether analog (OCH₃) |
| (9) | ethyl ether analog (OEt) |

-continued

| No. | Compound of Formula (V) |
|---|---|
| (10) | isopropyl ether analog |
| (11) | tert-butyl ether analog |
| (12) | benzyl ether analog (OCH₂Ph) |
| (13) | trityl ether analog (OCPh₃) |
| (14) | trimethylsilyl ether (OSiMe₃) |
| (15) | triethylsilyl ether (OSiEt₃) |
| (16) | tert-butyldimethylsilyl ether (OTBS) |
| (17) | tetrahydropyranyl ether (OTHP) |
| (18) | primary amide (CONH₂) analog |

| No. | Compound of Formula (V) |
|---|---|
| (19) | 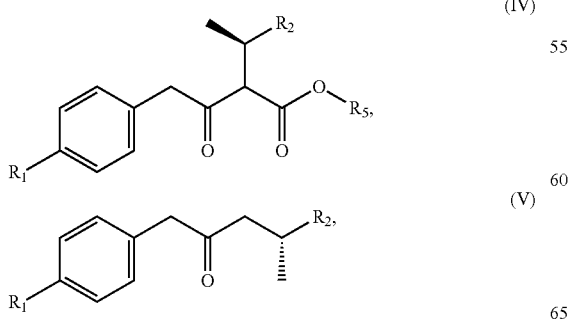 |
| (20) | |
| (21) | |
| (22) | |
| (23) | |

The compound of Formula (V) disclosed herein may be prepared by a deprotection reaction of a compound of Formula (IV):

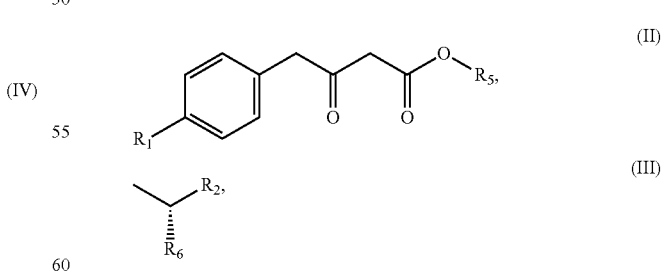

wherein
R$_1$ may be phenyl, methoxy, hydroxy, chloro, bromo, iodo, mesylate (—OMs), triflate (—OTf) or 4-methylbenzenesulfonate (—OTs) and in some embodiments, R$_1$ is phenyl;
R$_2$ may be

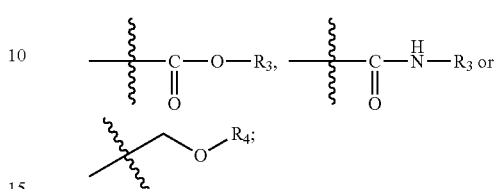

In some embodiments, R$_2$ is

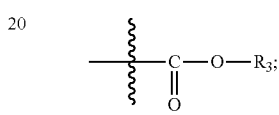

R$_3$ may be H, —(C$_1$-C$_4$)alkyl or —(C$_1$-C$_4$)alkyl-aryl; wherein —(C$_1$-C$_4$)alkyl in some embodiments may be methyl, ethyl, n-propyl, i-propyl, n-butyl, t-butyl; wherein —(C$_1$-C$_4$)alkyl-aryl in some embodiments may be benzyl or optionally substituted benzyl;
R$_4$ may be H, —(C$_1$-C$_4$)alkyl, —(C$_3$-C$_6$)heterocyclyl, —(C$_1$-C$_4$)alkyl-aryl, trimethylsilyl, triethylsilyl or t-butyldimethylsilyl; wherein —(C$_1$-C$_4$)alkyl in some embodiments may be methyl, ethyl, n-propyl, i-propyl, n-butyl, t-butyl; wherein —(C$_1$-C$_4$)alkyl-aryl in some embodiments may be benzyl or optionally substituted benzyl;
R$_5$ may be H, —(C$_1$-C$_4$)alkyl or —(C$_1$-C$_4$)alkyl-aryl; wherein —(C$_1$-C$_4$)alkyl in some embodiments may be methyl, ethyl, n-propyl, i-propyl, n-butyl, t-butyl; wherein —(C$_1$-C$_4$)alkyl-aryl in some embodiments may be benzyl or optionally substituted benzyl.

In some embodiments, the compound of Formula (V) is prepared by a deprotection reaction of the compound of Formula (IV) in the presence of a base or an acid. In certain embodiments, the acid is trifluoroacetic acid. In some embodiments, the base is lithium hydroxide.

The compound of Formula (IV) disclosed herein may be prepared by a substitution reaction of a compound of Formula (II) with a compound of Formula (III):

wherein
R$_1$, R$_2$ and R$_5$ may be the groups as defined above;
R$_6$ may be triflate (—OTf), mesylate (—OMs) or 4-methylbenzenesulfonate (—OTs).
Chiral methyl may be introduced by a substitution reaction of the compound of Formula (II) with the compound of Formula (III), and thus the compound of Formula (IV) can be obtained. In some embodiments, the substitution reaction is carried out in the presence of a strong base; In some embodiments, the strong base is sodium hydride.

The compound of Formula (II) may be prepared by a condensation reaction of a compound of Formula (I):

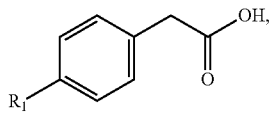
(I)

wherein $R_1$ may be the groups as defined above.

In some embodiments, wherein the compound of Formula (II) is prepared by a condensation reaction of the compound of Formula (I) with N,N'-carbonyldiimidazole and a compound of Formula (VIII):

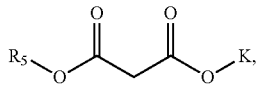
(VIII)

in the presence of magnesium chloride and triethylamine, wherein $R_5$ may be the groups as defined above.

In some embodiments, the compound of Formula (II) is prepared by a condensation reaction of the compound of Formula (I) with Meldrum's acid, 4-dimethylaminopyridine, $R_5$OH and pivaloyl chloride in the presence of N,N-diisopropylethylamine, wherein $R_5$ may be the groups as defined above.

In some embodiments, the method of preparing a compound of Formula (V) disclosed herein comprises the following steps:

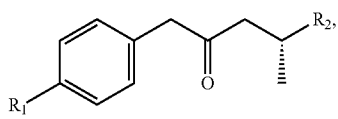
(V)

wherein $R_1$ is phenyl;
$R_2$ is

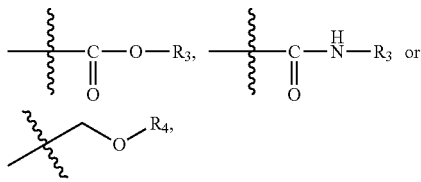

wherein $R_3$ may be H, methyl, ethyl, propyl, i-propyl, n-butyl, t-butyl or benzyl, and wherein $R_4$ is H, methyl, ethyl, propyl, i-propyl, n-butyl, t-butyl, benzyl, trimethylsilyl, triethylsilyl, t-butyldimethylsilyl, triphenylmethyl, tetrahydropyranyl;

a) preparing a compound of Formula (II) by a condensation reaction of a compound of Formula (I) in the presence of a base;

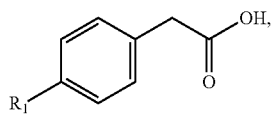
(I)

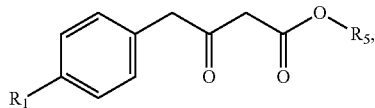
(II)

wherein:
$R_1$ is phenyl;
$R_5$ is H, methyl, ethyl, n-propyl, i-propyl, n-butyl or benzyl;

b) preparing a compound of Formula (IV) by a substitution reaction of the compound of Formula (II) with a compound of Formula (III) in the presence of a strong base;

(III)

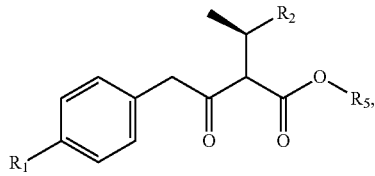
(IV)

wherein
$R_1$ is phenyl;
$R_2$ is

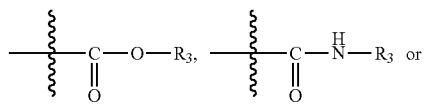

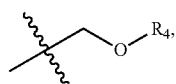

wherein $R_3$ may be H, methyl, ethyl, n-propyl, i-propyl, n-butyl, t-butyl or benzyl, and wherein $R_4$ is H, methyl, ethyl, n-propyl, i-propyl, n-butyl, t-butyl, benzyl, trimethylsilyl, triethylsilyl or t-butyldimethylsilyl;

$R_5$ may be H, methyl, ethyl, propyl, i-propyl, n-butyl or benzyl;

$R_6$ may be triflate (—OTf), mesylate (—OMs) or 4-methylbenzenesulfonate (—OTs);

c) preparing the compound of Formula (V) by a deprotection reaction of the compound of Formula (IV) in the presence of a base or an acid.

The synthetic route of preparing the compound of Formula (V) disclosed herein is depicted as follows:

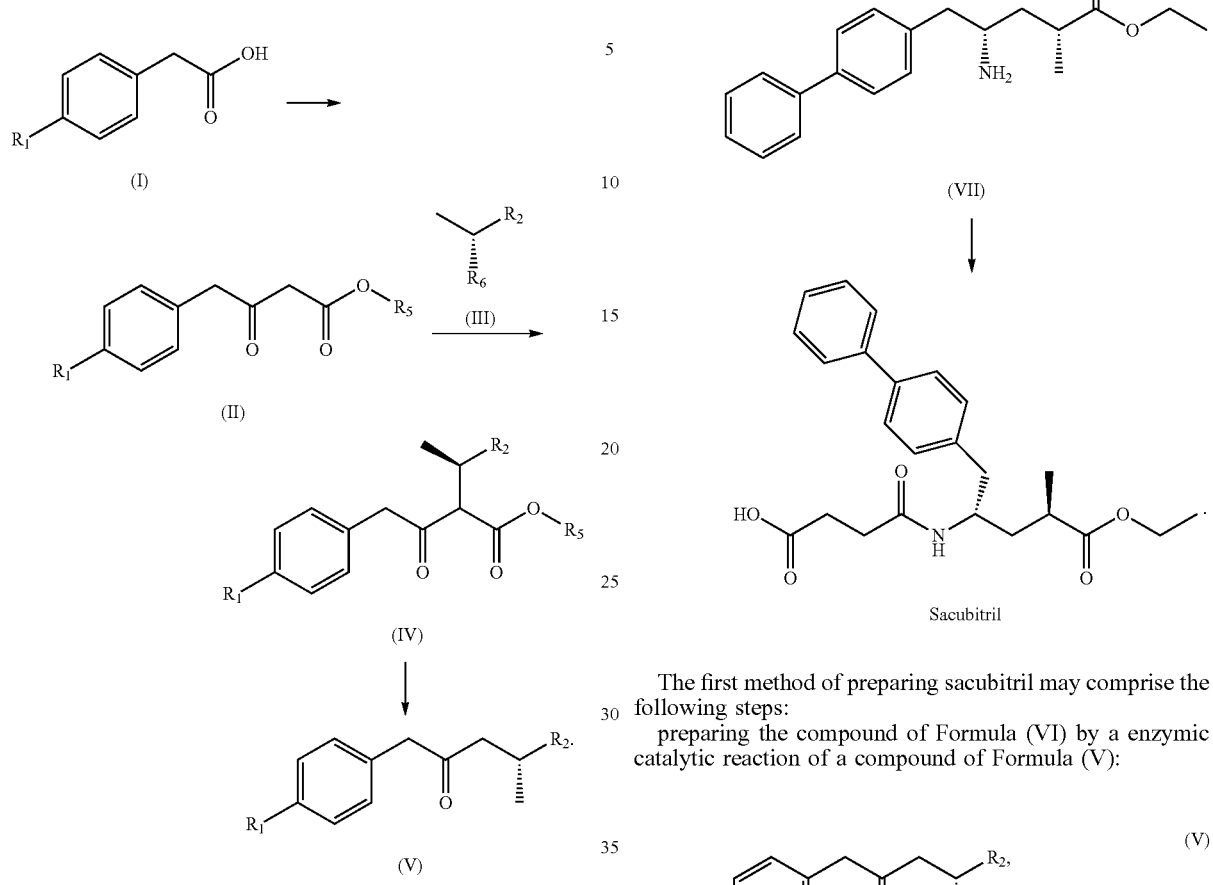

Under the inventive concept of the invention, those skilled in the art can adjust the reaction conditions appropriately, such as selecting other suitable reaction solvents, adjusting the reaction temperature, and prolonging the reaction time to obtain better reaction results and so on according to the present disclosure based on the method for preparing the compound of Formula (V) or an intermediate thereof disclosed herein. The compound of Formula (V) can be obtained by the above preparation method.

In second aspect, provided herein also are two methods for preparing sacubitril.

The first method of preparing sacubitril from the compound of Formula (V) may be depicted in the following scheme:

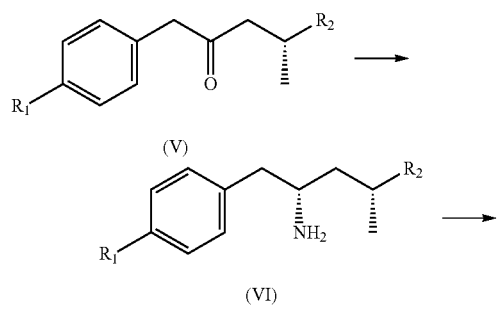

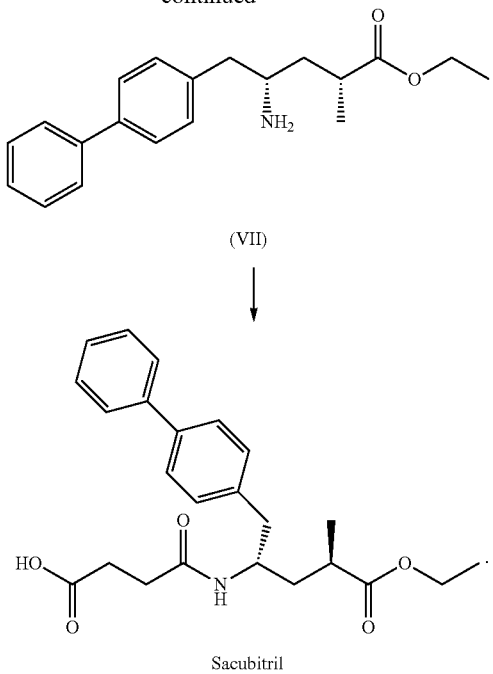

The first method of preparing sacubitril may comprise the following steps:

preparing the compound of Formula (VI) by a enzymic catalytic reaction of a compound of Formula (V):

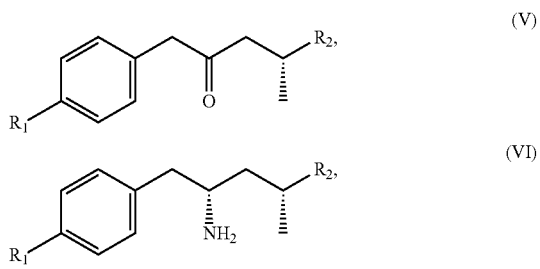

wherein $R_1$ is phenyl, methoxy, hydroxy, chloro, bromo, iodo, mesylate, triflate or 4-methylbenzenesulfonate;

$R_2$ is

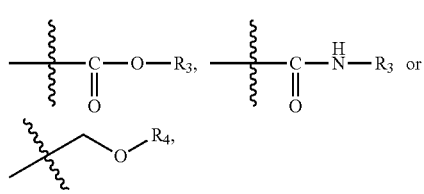

$R_3$ is H, —($C_1$-$C_4$)alkyl or —($C_1$-$C_4$)alkyl-aryl;

$R_4$ is H, —($C_1$-$C_4$)alkyl, —($C_3$-$C_6$)heterocyclyl, —($C_1$-$C_4$)alkyl-aryl, trimethylsilyl, triethylsilyl or t-butyldimethylsilyl.

The first method of preparing sacubitril may comprise the following steps:

a) preparing a compound of Formula (VI) by an enzymic catalytic reaction of a compound of Formula (V),

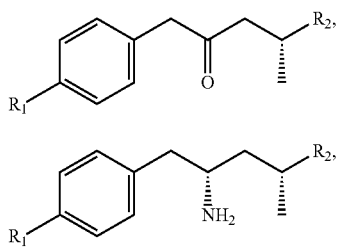

(V)

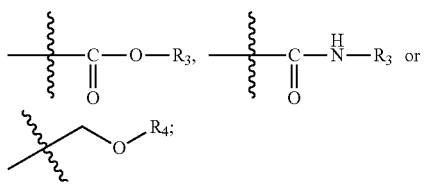

(VI)

wherein
R₁ may be phenyl, methoxy, hydroxy, chloro, bromo, iodo, mesylate (—OMs), triflate (—OTf) or 4-methylbenzenesulfonate (—OTs);

R₂ may be

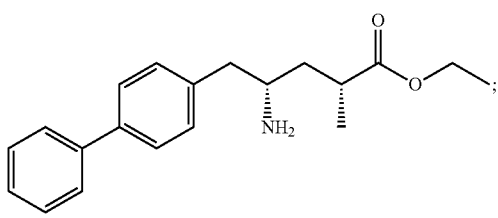

R₃ may be H, —(C₁-C₄)alkyl or —(C₁-C₄)alkyl-aryl; wherein —(C₁-C₄)alkyl in some embodiments may be methyl, ethyl, n-propyl, i-propyl, n-butyl, t-butyl; wherein —(C₁-C₄)alkyl-aryl in some embodiments may be benzyl or optionally substituted benzyl;

R₄ may be H, —(C₁-C₄)alkyl, —(C₃-C₆)heterocyclyl, —(C₁-C₄)alkyl-aryl, trimethylsilyl, triethylsilyl or t-butyldimethylsilyl; wherein —(C₁-C₄)alkyl in some embodiments may be methyl, ethyl, n-propyl, i-propyl, n-butyl, t-butyl; wherein —(C₁-C₄)alkyl-aryl in some embodiments may be benzyl or optionally substituted benzyl;

b) optionally, preparing a compound of Formula (VII) from the compound of Formula (VI),

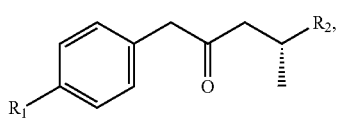

(VII)

c) preparing sacubitril from the compound of Formula (VII).

In some embodiments, the first method of preparing sacubitril may comprise the following steps:

a) preparing a compound of Formula (VI) by an enzymic catalytic reaction of a compound of Formula (V), (V)

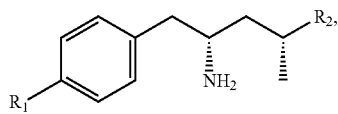

(VI)

wherein R₁ is phenyl,

R₂ is

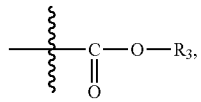

R₃ is H, —(C₁-C₄)alkyl or —(C₁-C₄)alkyl-aryl; wherein —(C₁-C₄)alkyl in some embodiments may be methyl, ethyl, n-propyl, i-propyl, n-butyl, t-butyl; wherein —(C₁-C₄)alkyl-aryl in some embodiments may be benzyl or optionally substituted benzyl;

b) optionally, preparing a compound of Formula (VII) from the compound of Formula (VI),

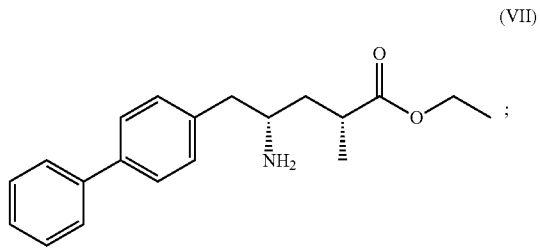 [SMILES: CCOC(=O)[C@H](C)C[C@H](N)Cc1ccc(-c2ccccc2)cc1]

(VII)

c) preparing sacubitril from the compound of Formula (VII).

In some embodiments, the first method of preparing sacubitril may comprise the following steps:

a) preparing a compound of Formula (VII) by an enzymic catalytic reaction of a compound of Formula (V),

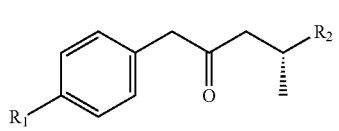

(V)

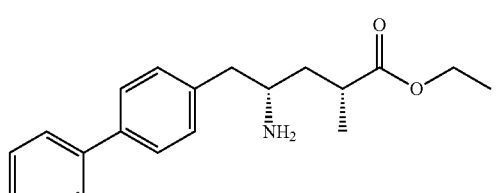

(VII)

wherein R₁ is phenyl, wherein $R_2$ is

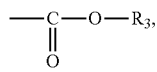

$R_3$ is ethyl;

b) preparing sacubitril by an amide condensation reaction of the compound of Formula (VII) with succinic anhydride.

In some embodiments, in the above preparation method of sacubitril, wherein the enzymic catalytic reaction is carried out in the presence of ω-transaminase and phosphopyridoxal.

In some embodiments, in the above preparation method of sacubitril, wherein the compound of Formula (VII) may be prepared by a hydrolysis reaction of the compound of Formula (VI) and then an esterification reaction of the hydrolysis product with ethanol.

The second method of preparing sacubitril from the compound of Formula (V) may be depicted in the following scheme:

wherein $R_1$ is phenyl, methoxy, hydroxy, chloro, bromo, iodo, mesylate, triflate or 4-methylbenzenesulfonate;

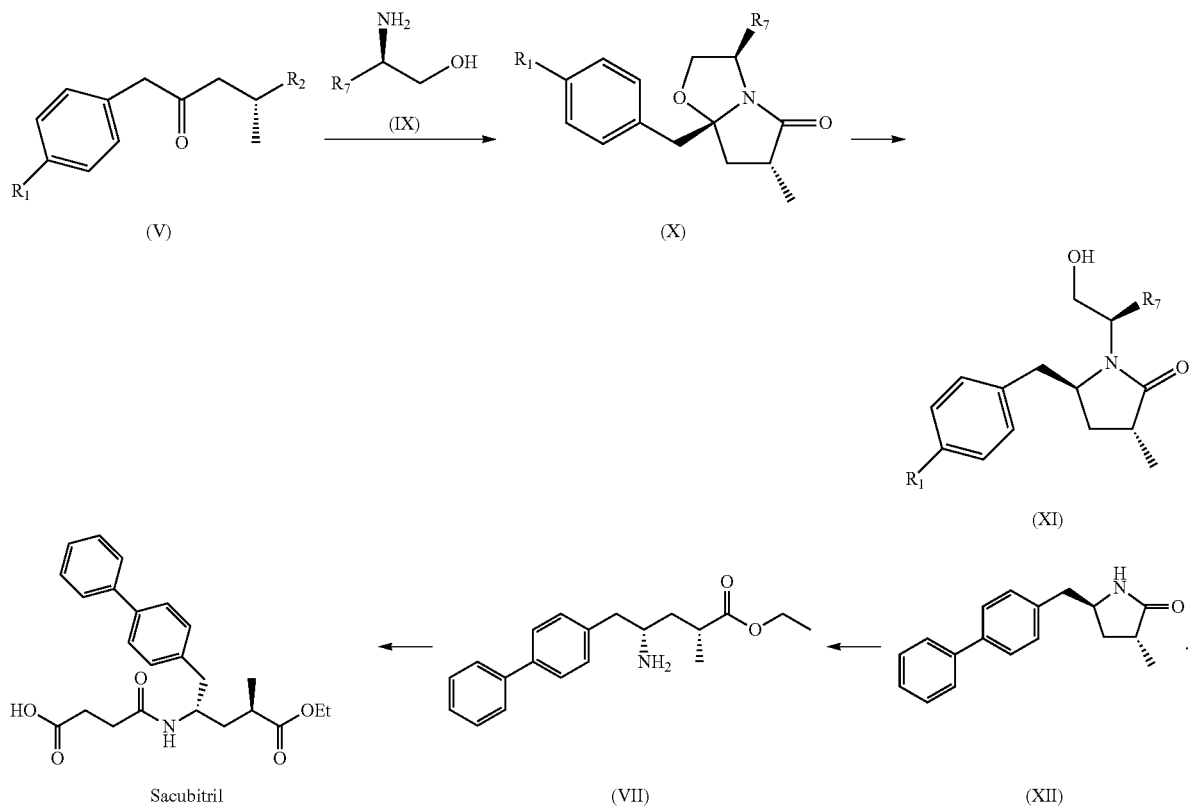

The second method of preparing sacubitril may comprise the following steps:

preparing a compound of Formula (X) by a reaction of a compound of Formula (V) with a compound of Formula (IX),

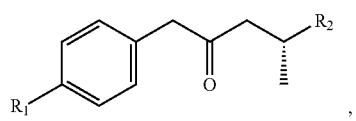

$R_2$ is

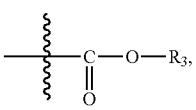

$R_3$ is H, —($C_1$-$C_4$)alkyl or —($C_1$-$C_4$)alkyl-aryl,
$R_7$ is phenyl, —($C_1$-$C_4$)alkyl or —($C_1$-$C_4$)alkyl-aryl.

The second method of preparing sacubitril may comprise the following steps: preparing a compound of Formula (XI) from the compound of Formula (X):

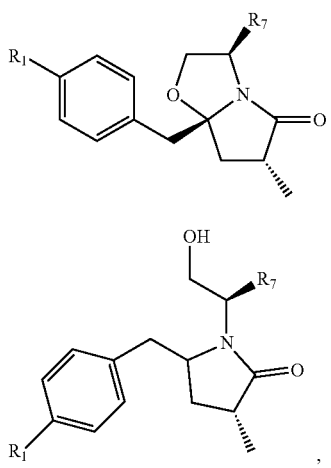

wherein

R₁ is phenyl, methoxy, hydroxy, chloro, bromo, iodo, mesylate, triflate or 4-methylbenzenesulfonate; and R₇ is phenyl, —(C₁-C₄)alkyl or —(C₁-C₄)alkyl-aryl.

The second method of preparing sacubitril may comprise the following steps:

a) preparing a compound of Formula (X) by a reaction of a compound of Formula (V) with a compound of Formula (IX),

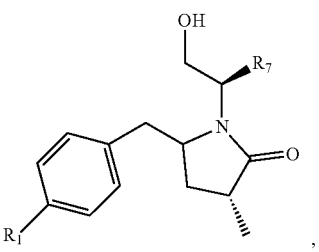

wherein

R₁ may be phenyl, methoxy, hydroxy, chloro, bromo, iodo, mesylate (—OMs), triflate (—OTf) or 4-methylbenzenesulfonate (—OTs);

R₂ may be

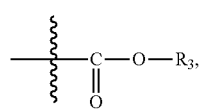

R₃ may be H, —(C₁-C₄)alkyl or —(C₁-C₄)alkyl-aryl; wherein —(C₁-C₄)alkyl in some embodiments may be methyl, ethyl, n-propyl, i-propyl, n-butyl, t-butyl; wherein —(C₁-C₄)alkyl-aryl in some embodiments may be benzyl or optionally substituted benzyl;

R₇ may be phenyl, —(C₁-C₄)alkyl or —(C₁-C₄)alkyl-aryl; wherein —(C₁-C₄)alkyl in some embodiments may be methyl, ethyl, n-propyl, i-propyl, n-butyl, t-butyl; wherein —(C₁-C₄)alkyl-aryl in some embodiments may be benzyl or optionally substituted benzyl;

b) preparing a compound of Formula (XI) from the compound of Formula (X):

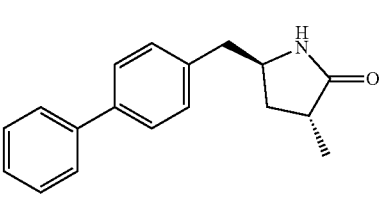

R₁ and R₇ are as defined in step a);

c) preparing a compound of Formula (XII) from the compound of Formula (XI):

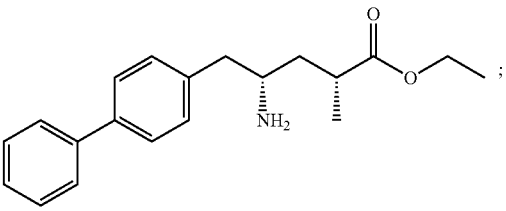

d) preparing a compound of Formula (VII) from the compound of Formula (XII):

and e) preparing sacubitril from the compound of Formula (VII).

In some embodiments, the compound of Formula (IX) is D-phenylglycinol.

In some embodiments, the compound of Formula (XI) is prepared from the compound of Formula (X) in the presence of titanium tetrachloride and triethyl silicane.

In some embodiments, the compound of Formula (XII) is prepared from the compound of Formula (XI) in the presence of palladium on carbon (Pd/C).

In some embodiments, the compound of Formula (VII) is prepared from the compound of Formula (XII) in ethanol in the presence of an acid. In some embodiments, the acid is hydrochloric acid.

In some embodiments, the second method of preparing sacubitril comprises the following steps:

a) preparing a compound of Formula (XIII) by a reaction of (R)-5-([1,1'-biphenyl]-4-yl)-2-methyl-4-oxopentanoic acid with D-phenylglycinol (as mentioned above compound (1)),

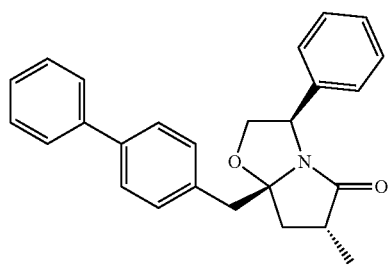

(XIII)

b) preparing a compound of Formula (XIV) from the compound of Formula (XIII) in the presence of titanium tetrachloride and triethyl silicane,

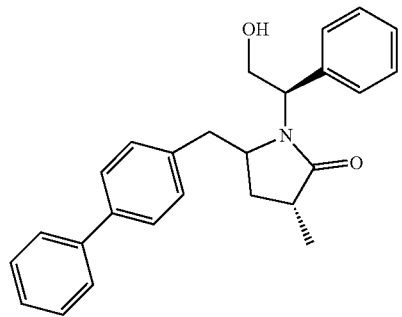

(XIV)

c) preparing a compound of Formula (XII) from the compound of Formula (XIV) using palladium on carbon (Pd/C) as a catalyst,

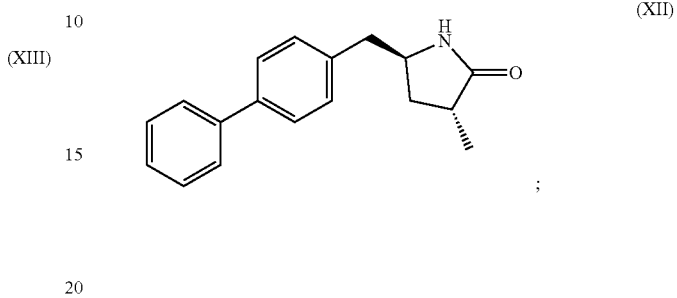

(XII)

d) preparing a compound of Formula (VII) by a ring opening reaction of the compound of Formula (XII):

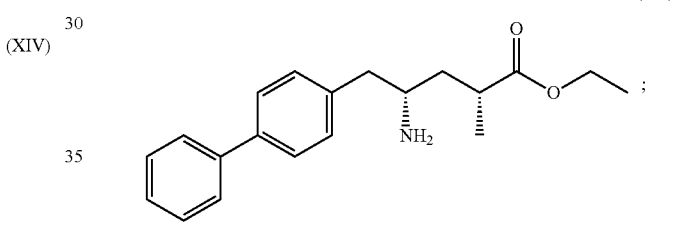

(VII)

and e) preparing sacubitril from the compound of Formula (VII);

The reaction route is shown as follows:

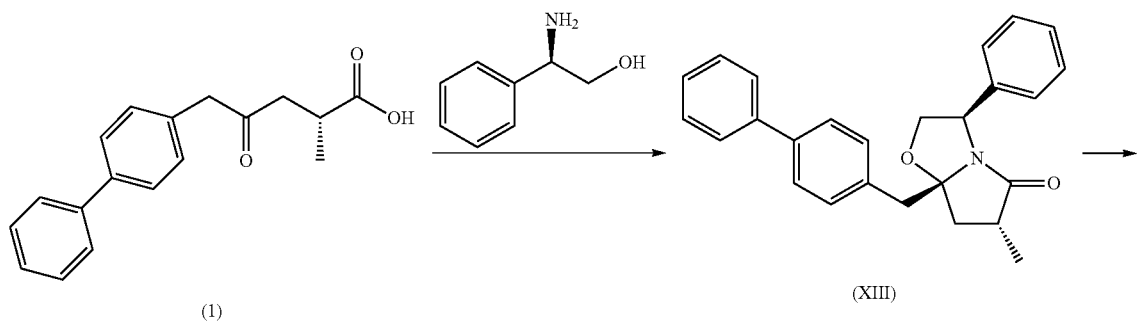

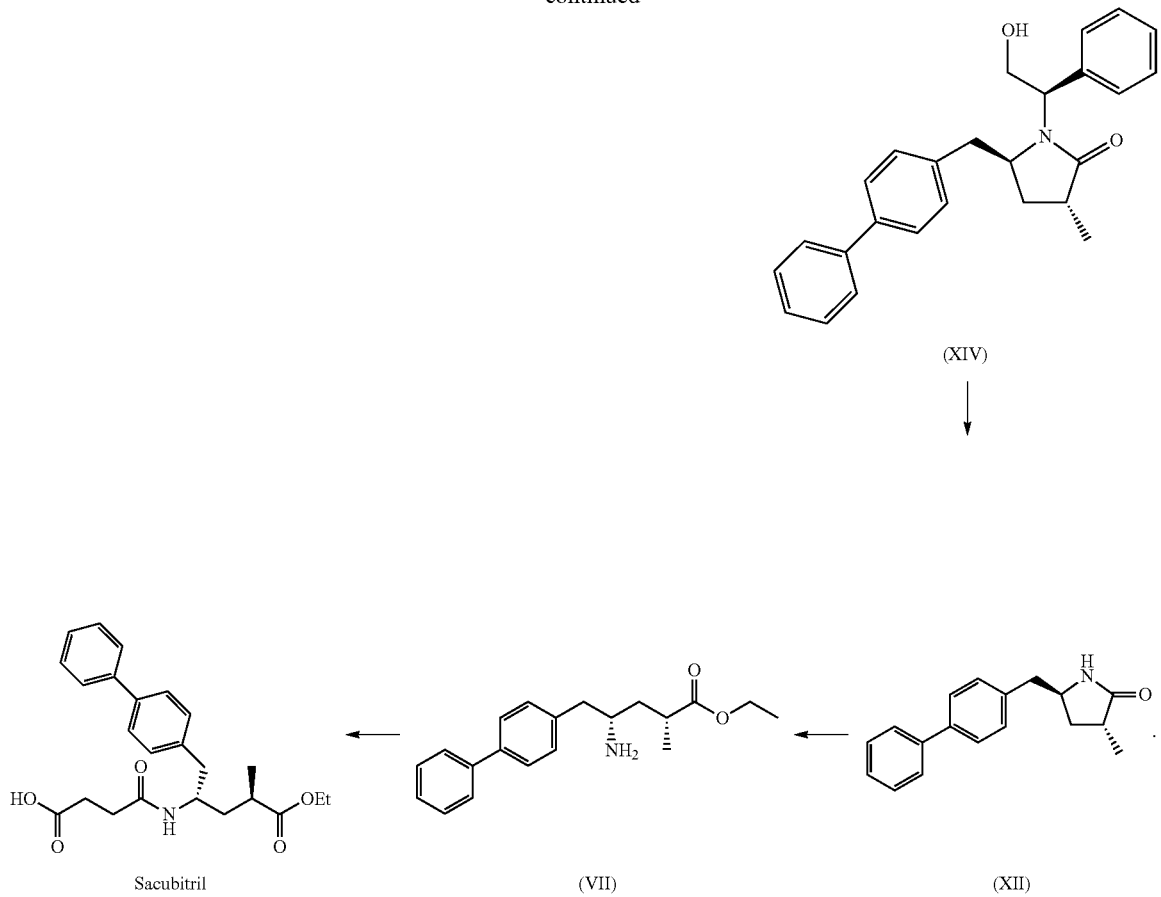

In the method of preparing sacubitril disclosed herein, sacubitril was prepared by an amide condensation reaction of ((2R,4S)-ethyl 5-([1,1'-biphenyl]-4-yl)-4-amino-2-methylpentanoate) represented by the compound of Formula (VII) with butanedioic anhydride in the presence of a base; the step was disclosed in prior art, such as in both WO 2008031567 A1 and CN 104557600 A, it is known to the persons skilled in the art.

The technology provided herein compared with prior art has advantages as follows:

It provides a completely new sacubitril intermediate (V) and a preparation method thereof, the intermediate was prepared by using a low cost readily available raw material biphenyl acetic acid, and suffering from three steps of condensation, substitution, deprotection to get intermediate (V), each step has a high yield and simple operation; the intermediate has a similar parent structure as sacubitril, at present, no similar structures as this have been reported, and no methods of preparing sacubitril using a similar structure as an intermediate have been reported;

It provides a method of preparing sacubitril using intermediate (V) as the raw material and enzyme catalyzed reaction as a key step; In this route, a chiral amino was introduced with high yield and high stereoselectivity in one step under enzymatic catalysis, the reaction conditions were mild, the shortest route can give sacubitril within two steps; The introduction method of the chiral amino group in the prior art generally requires a chiral raw material, a chiral induction reagent, a chiral catalyst or a chiral separation, and has some disadvantages of high cost, unfriendly environment, low yield, poor stereoselectivity, long route and need of repeated protection and deprotection, and other issues;

It provides a method of preparing sacubitril using intermediate (V) as the raw material and chiral substituted glycinol as the chiral auxiliary, comprising steps of cyclization, deprotection, ring opening and amidation, the method compared with the prior method, the chiral auxiliary was replaced by (S)-1-(t-aminobenzyl)-2-naphthol to substituted glycine, which is cheaper and more readily available, the preparation method of the raw material intermediate (V) is simple, and the reaction conditions in each step are mild and simple, and are suitable for industrial production.

EXAMPLES

In order to make persons skilled in the art understand the technical solutions of the present invention better, the present invention exemplarily provides a part of the preparation examples, the present invention will be explained in more detail below by using non-limiting examples.

The reagents used in the present invention are all commercially available or can be prepared by the methods described herein.

mL milliliter, g gram, h hour(s), N mol/L, 1H NMR H nuclear magnetic spectrometer, MS mass spectrometry, HPLC high Performance Liquid Chromatography, CDCl$_3$ deuterochloroform, DMSO-d$_6$ deuterated dimethyl sulfoxide.

Intermediate (V) and Preparation Method Thereof

Example 1. Preparation of (R)-5-([1,1'-biphenyl]-4-yl)-2-methyl-4-oxopentanoic Acid

Example 1-a: Preparation of Ethyl 4-([1,1'-biphenyl]-4-yl)-3-oxobutyrate

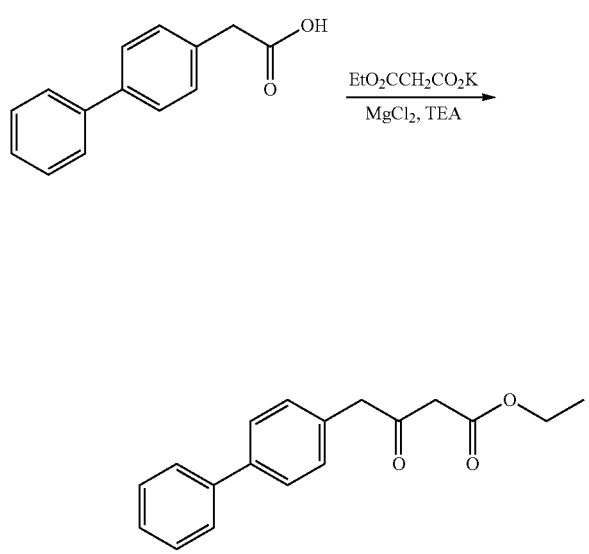

To a 500 mL three neck flask A were added 200 mL of ethyl acetate and 28.64 g of N,N'-carbonyldiimidazole at room temperature, and then 25.00 g of 4-biphenyl acetic acid was added in portions to flask A, the generation rate of gas was controlled. After the addition, the reaction liquid was heated to 45° C. and reacted for 3 hours, and then cooled to 20 to 30° C., the flask was evacuated for pressure reduction for 1 hour, and ready for use. To a 1 L flask B were added 280 mL of ethyl acetate, 28.06 g of ethyl potassium malonate ($EtO_2CCH_2COOK$) and 15.70 g of magnesium chloride ($MgCl_2$) at room temperature, the temperature was controlled at 20° C. to 30° C., and then 19.07 g of triethylamine (TEA) was added dropwise slowly. After the addition, the mixture was further stirred for 1 hour. To flask B was added the materials in flask A at room temperature, the mixture was heated to 45° C. and reacted for 16 hours. The reaction liquid was cooled to 20° C. to 30° C., and 180 mL of 4 N hydrochloric acid solution was added, and the mixture was partitioned, the organic layer was washed three times with 250 mL of 6.5% sodium bicarbonate aqueous solution each time, the organic layers were combined, the solvent was then stripped off in vacuo at 45° C. to give a yellow brown oil. To the obtained oil was added 150 mL of n-hexane, the mixture was stirred at 20° C. to 30° C. for 18 hours and filtered, the filter cake was washed with n-hexane and dried at 40° C. to 50° C. in vacuo for 5 hours to give ethyl 4-([1,1'-biphenyl]-4-yl)-3-oxobutyrate 26.3 g, the yield is 79.1%. $^1$H NMR (600 MHz, $CDCl_3$) δ 7.60 (dt, J=15.9, 6.1 Hz, 4H), 7.47 (t, J=7.7 Hz, 2H), 7.37 (dt, J=9.7, 7.9 Hz, 1H), 7.33-7.28 (m, 2H), 4.25-4.18 (m, 2H), 3.90 (s, 2H), 3.52 (s, 2H), 1.30 (t, J=7.1 Hz, 3H). ESI-MS (m/z): 283.3 ([M+H]+).

Example 1-b: Preparation of (3R)-1-ethyl-4-methyl 2-(2-([1,1'-biphenyl]-4-yl)acetyl)-3-methylsuccinate

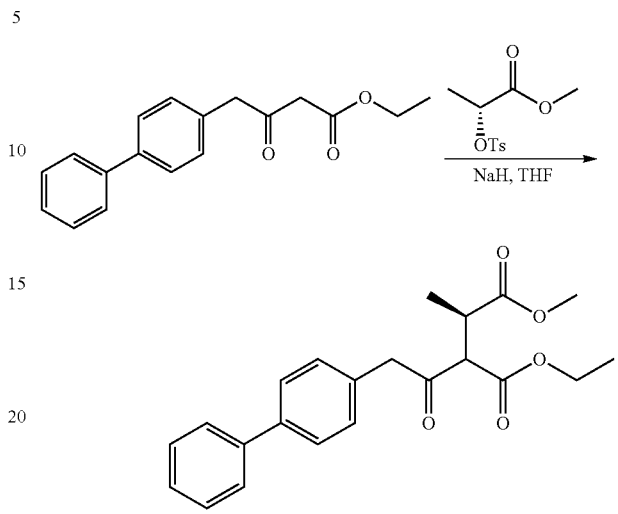

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of ethyl 4-([1,1'-biphenyl]-4-yl)-3-oxobutyrate in 100 mL of tetrahydrofuran (THF) was added dropwise slowly under nitrogen. After the addition, the reaction liquid was heated to 20° C. to 30° C. and stirred for additional 30 min. The reaction liquid was cooled to 0° C., and a solution of (R)-methyl-2-(4-methylbenzenesulfonate)propionate (31.37 g) in tetrahydrofuran (THF) (100 mL) was added dropwise slowly, after the addition, the reaction liquid was heated to 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, and then concentrated to give an oil (3R)-1-ethyl-4-methyl 2-(2-([1,1'-biphenyl]-4-yl)acetyl)-3-methylsuccinate 48.60 g, which was used in the next step without further purification.

Example 1-c: Preparation of (R)-5-([1,1'-biphenyl]-4-yl)-2-methyl-4-oxopentanoic Acid

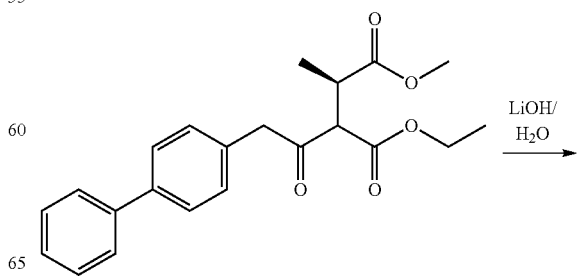

-continued

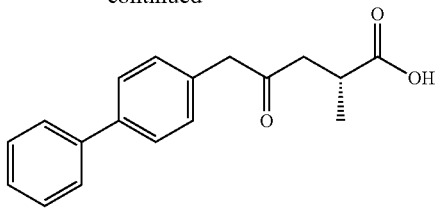

To a 500 mL flask were added 13.04 g of (3R)-1-ethyl-4-methyl 2-(2-([1,1'-biphenyl]-4-yl)acetyl)-3-methylsuccinate and 130 mL of tetrahydrofuran (THF), the reaction liquid was cooled to 0° C., a solution of 3.71 g of lithium hydroxide monohydrate (LiOH—H$_2$O) in 130 mL of water was added dropwise slowly. After the addition, the reaction liquid was heated to 60° C. to 70° C. and stirred for additional 16 hours. After the raw materials were consumed completely monitored by HPLC, the reaction liquid was cooled to 20° C. to 30° C., 100 mL of 1 N hydrochloric acid was added dropwise slowly to adjust pH to 2-3, and the reaction liquid was extracted with ethyl acetate 2 times, each time with 100 mL. The organic layers were combined and concentrated to give an oil (R)-5-([1,1'-biphenyl]-4-yl)-2-methyl-4-oxopentanoic acid 8.50 g, the yield was 85.1%. $^1$H NMR (600 MHz, DMSO-d$_6$) δ 12.16 (s, 1H), 7.66 (d, J=7.3 Hz, 2H), 7.61 (d, J=8.1 Hz, 2H), 7.46 (t, J=7.7 Hz, 2H), 7.36 (t, J=7.4 Hz, 1H), 7.28 (d, J=8.1 Hz, 2H), 3.82 (s, 2H), 2.88 (dd, J=17.7, 8.1 Hz, 1H), 2.76-2.69 (m, 1H), 2.61 (dd, J=17.7, 5.4 Hz, 1H), 1.05 (dd, J=16.4, 7.1 Hz, 3H). ESI-MS (m/z): 283.3 ([M+H]+).

Example 2. Preparation of (R)-methyl 5-([1,1'-biphenyl]-4-yl)-2-methyl-4-oxopentanoate Example 2-a: Preparation of t-butyl 4-([1,1'-biphenyl]-4-yl)-3-oxobutyrate

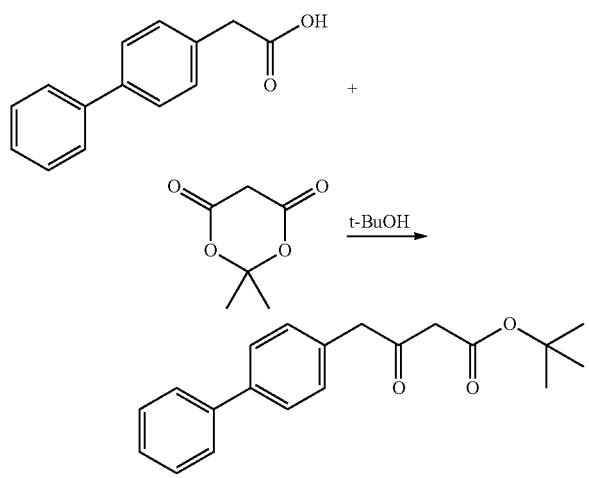

To a 500 mL flask were added 10.61 g of 4-biphenylacetic acid, 8.65 g of Meldrum's acid, 0.61 g of 4-dimethylaminopyridine (DMAP) and 80 mL of dimethylacetamide (DMAC) at room temperature in turn, the mixture was stirred to dissolution. To the reaction liquid was added 13.57 g of N,N-diisopropylethylamine (DIPEA) dropwise slowly, after the addition, 6.63 g of pivaloyl chloride was added dropwise slowly and then the mixture was heated to 50° C. and stirred for 20 hours. To the reaction liquid was added 18.5 g of t-butyl alcohol (t-BuOH), and the mixture was heated to 100° C. for 7 hours. After the raw materials were consumed completely monitored by HPLC, the reaction liquid was cooled to 20° C. to 30° C., 200 mL of water was added, and the reaction liquid was extracted with ethyl acetate 3 times, each time with 100 mL. The organic layers were combined and concentrated to give t-butyl 4-([1,1'-biphenyl]-4-yl)-3-oxobutyrate 13.34 g, the yield was 86%. $^1$H NMR (600 MHz, CDCl$_3$) δ 7.57 (t, J=6.8 Hz, 4H), 7.43 (t, J=7.4 Hz, 2H), 7.38-7.32 (m, 1H), 7.31-7.25 (m, 2H), 3.87 (s, 2H), 3.41 (s, 2H), 1.47 (s, 9H). ESI-MS (m/z): 311.4 ([M+H]+).

Example 2-b: Preparation of (3R)-1-t-butyl-4-methyl-2-(2-([1,1'-biphenyl]-4-yl)acetyl)-3-methylsuccinate

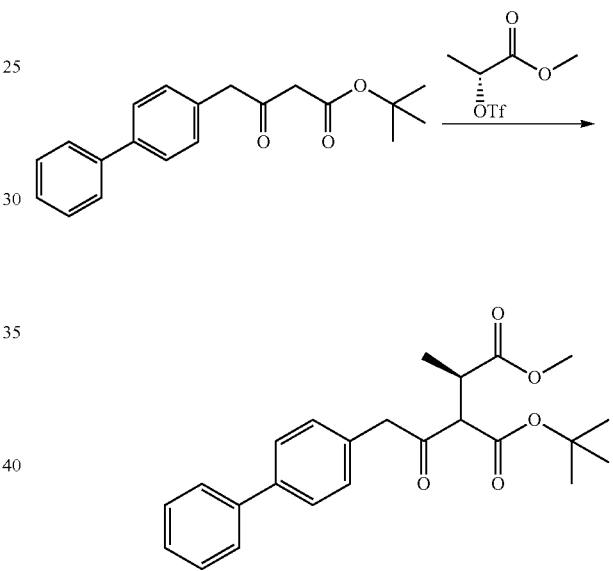

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of t-butyl 4-([1,1'-biphenyl]-4-yl)-3-oxobutyrate in 100 mL of tetrahydrofuran was added dropwise slowly under nitrogen. After the addition, the reaction liquid was heated to 20° C. to 30° C. and stirred for additional 30 min. The reaction liquid was cooled to 0° C., and a solution of 31.37 g of (R)-methyl-2-(triflate)propionate in 100 mL of tetrahydrofuran was added dropwise slowly, after the addition, the reaction liquid was heated to 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, then concentrated to give an oil (3R)-1-t-butyl-4-methyl 2-(-2-([1,1'-biphenyl]-4-yl)acetyl)-3-methylsuccinate 48.60 g, which was used in the next step without further purification.

Example 2-c: Preparation of (R)-methyl 5-([1,1'-biphenyl]-4-yl)-2-methyl-4-oxopentanoate

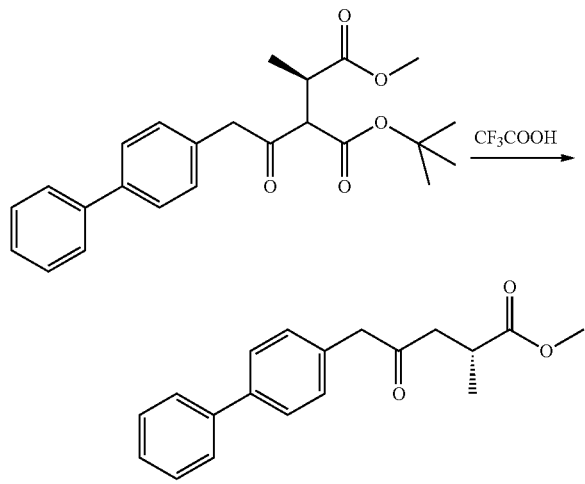

To a 100 mL flask were added 6.00 g of (3R)-1-t-butyl-4-methyl-2-(2-([1,1'-biphenyl]-4-yl)acetyl)-3-methylsuccinate, 30 mL of dichloromethane (DCM) and 11.01 g of trifluoroacetic acid (CF$_3$COOH), the mixture was heated to 42° C. with stirring and reacted for 22 hours. After the raw materials were consumed completely monitored by HPLC, to the reaction liquid was added 150 mL of 6.5% sodium bicarbonate solution dropwise slowly, and 150 mL of 2 N hydrochloric acid was added to adjust pH to 2-3, and the reaction liquid was extracted with ethyl acetate 3 times, each time with 100 mL. The organic layers were combined and washed 2 times with 200 mL each time of water, then concentrated to give an oil (R)-methyl 5-([1,1'-biphenyl]-4-yl)-2-methyl-4-oxopentanoate 4.10 g, the yield was 91.5%. $^1$H NMR (400 MHz, CDCl$_3$) δ 7.60 (t, J=7.7 Hz, 4H), 7.46 (t, J=7.6 Hz, 2H), 7.37 (t, J=7.3 Hz, 1H), 7.30 (d, J=8.1 Hz, 2H), 3.78 (s, 2H), 3.69 (s, 3H), 3.04-2.94 (m, 2H), 2.60-2.51 (m, 1H), 1.18 (d, J=6.8 Hz, 3H). ESI-MS (m/z): 297.3 ([M+H]+).

Example 3. Preparation of (R)-ethyl 5-([1,1'-biphenyl]-4-yl)-2-methyl-4-oxopentanoate

Example 3-a: Preparation of t-butyl 4-([1,1'-biphenyl]-4-yl)-3-oxobutyrate

The procedure is the same as the procedure of Example 2-a.

Example 3-b: Preparation of (3R)-1-t-butyl-4-ethyl-2-(2-([1,1'-biphenyl]-4-yl)acetyl)-3-methylsuccinate

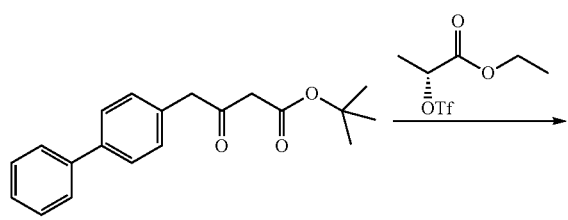

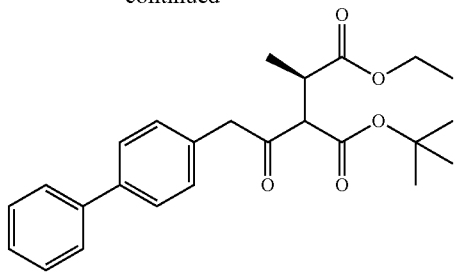

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of t-butyl 4-([1,1'-biphenyl]-4-yl)-3-oxobutyrate in 100 mL of tetrahydrofuran was added dropwise slowly under nitrogen. After the addition, the reaction liquid was heated to a temperature of 20° C. to 30° C. and stirred for additional 30 min. The reaction liquid was cooled to 0° C., and a solution of 33.37 g of (R)-ethyl-2-(triflate)propionate in 100 mL of tetrahydrofuran was added dropwise slowly, after the addition, the reaction liquid was heated to a temperature of 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, then concentrated to give an oil (3R)-1-t-butyl-4-ethyl 2-(-2-([1,1'-biphenyl]-4-yl)acetyl)-3-methylsuccinate 49.60 g, which was used in the next step without further purification.

Example 3-c: Preparation of (R)-ethyl 5-([1,1'-biphenyl]-4-yl)-2-methyl-4-oxopentanoate

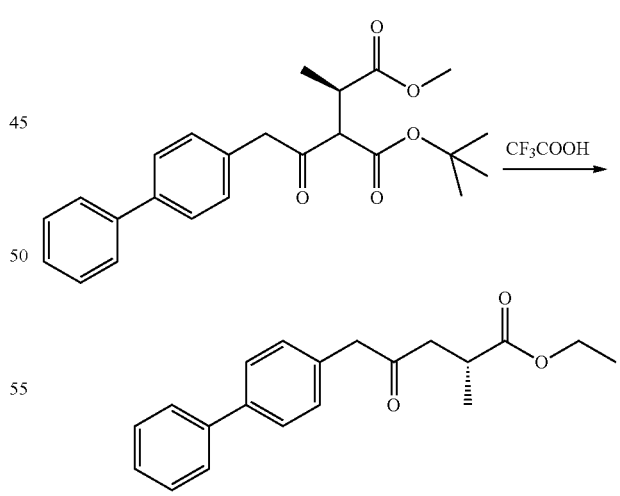

To a 100 mL flask were added 6.00 g of (3R)-1-t-butyl-4-ethyl-2-(2-([1,1'-biphenyl]-4-yl)acetyl)-3-methylsuccinate, 30 mL of dichloromethane (DCM) and 11.01 g of trifluoroacetic acid (CF$_3$COOH), the mixture was heated to 42° C. with stirring and reacted for 22 hours. After the raw materials were consumed completely monitored by HPLC, to the reaction liquid was added 150 mL of 6.5% sodium bicarbonate solution dropwise slowly, and 150 mL of 2 N hydrochloric acid was added to adjust pH to 2-3, and the reaction liquid was extracted with ethyl acetate 3 times, each time with 100 mL. The organic layers were combined and washed 2 times with 200 mL each time of water, then concentrated in vacuo to give an oil (R)-ethyl 5-([1,1'-biphenyl]-4-yl)-2-methyl-4-oxopentanoate 4.17 g, the yield was 92%. $^1$H NMR (400 MHz, CDCl$_3$) δ 7.60 (t, J=7.7 Hz, 4H), 7.47 (t, J=7.7 Hz, 2H), 7.37 (t, J=7.3 Hz, 1H), 7.30 (d, J=8.1 Hz, 2H), 4.06 (q, J=7.1 Hz, 2H), 3.78 (s, 2H), 3.04-2.94 (m, 2H), 2.60-2.51 (m, 1H), 1.20-1.15 (m, 6H). ESI-MS (m/z): 311.4 ([M+H]+).

Example 4. Preparation of (R)-isopropyl-benzyl-5-([1,1'-biphenyl]-4-yl)-2-methyl-4-oxopentanoate Example 4-a: Preparation of t-butyl 4-([1,1'-biphenyl]-4-yl)-3-oxobutyrate The procedure is the same as the procedure of Example 2-a.

Example 4-b: Preparation of (3R)-1-t-butyl-4-isopropyl-2-(2-([1,1'-biphenyl]-4-yl)acetyl)-3-methylsuccinate

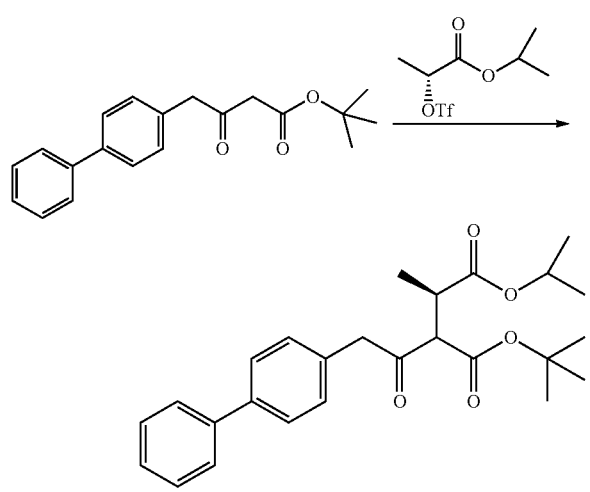

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of t-butyl 4-([1,1'-biphenyl]-4-yl)-3-oxobutyrate in 100 mL of tetrahydrofuran was added dropwise slowly under nitrogen. After the addition, the reaction liquid was heated to a temperature of 20° C. to 30° C. and stirred for additional 30 min. The reaction liquid was cooled to 0° C., and a solution of 33.37 g of (R)-isopropyl-2-(triflate)propionate in 100 mL of tetrahydrofuran was added dropwise slowly, after the addition, the reaction liquid was heated to a temperature of 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, then concentrated in vacuo to give an oil (3R)-1-t-butyl-4-isopropyl-2-(-2-([1,1'-biphenyl]-4-yl)acetyl)-3-methylsuccinate 50.60 g, which was used in the next step without further purification.

Example 4-c: Preparation of (R)-isopropyl benzyl-5-([1,1'-biphenyl]-4-yl)-2-methyl-4-oxopentanoate

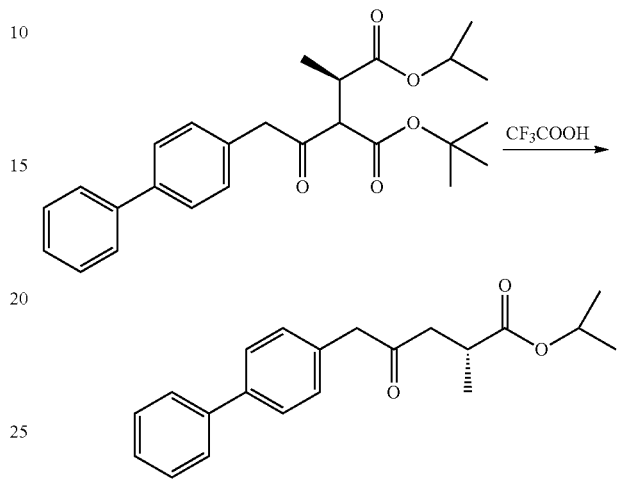

To a 100 mL flask were added 6.00 g of (3R)-1-t-butyl-4-isopropyl-2-(2-([1,1'-biphenyl]-4-yl)acetyl)-3-methylsuccinate, 30 mL of dichloromethane (DCM) and 11.01 g of trifluoroacetic acid (CF$_3$COOH), the mixture was heated to 42° C. with stirring and reacted for 22 hours. After the raw materials were consumed completely monitored by HPLC, to the reaction liquid was added 150 mL of 6.5% sodium bicarbonate solution dropwise slowly, and 150 mL of 2 N hydrochloric acid was added to adjust pH to 2-3, and the reaction liquid was extracted with ethyl acetate 3 times, each time with 100 mL. The organic layers were combined and washed 2 times with 200 mL each time of water, then concentrated in vacuo to give an oil (R)-isopropyl 5-([1,1'-biphenyl]-4-yl)-2-methyl-4-oxopentanoate 3.80 g, the yield was 83.0%. $^1$H NMR (600 MHz, CDCl$_3$) δ 7.60 (dt, J=15.9, 6.1 Hz, 4H), 7.47 (t, J=7.7 Hz, 2H), 7.37 (dt, J=9.7, 7.9 Hz, 1H), 7.33-7.28 (m, 2H), 4.93 (m, 1H), 3.78 (s, 2H), 3.04-2.94 (m, 2H), 2.60-2.51 (m, 1H), 1.30 (d, J=7.1 Hz, 6H), 1.18 (d, J=6.8 Hz, 3H). ESI-MS (m/z): 325.4 ([M+H]+).

Example 5. Preparation of (R)-benzyl-benzyl-5-([1,1'-biphenyl]-4-yl)-2-methyl-4-oxopentanoate Example 5-a: Preparation of t-butyl 4-([1,1'-biphenyl]-4-yl)-3-oxobutyrate

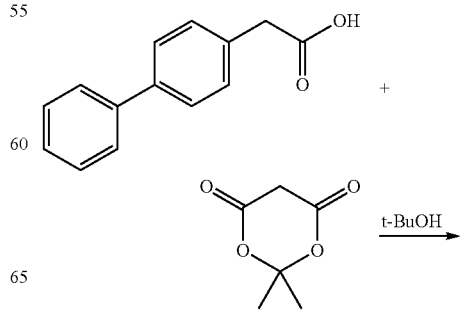

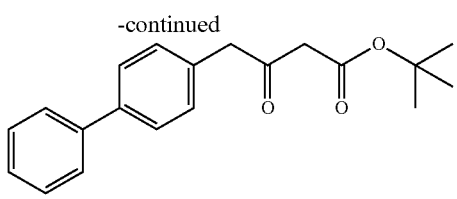

To a 1 L flask were added 20.00 g of 4-biphenylacetic acid, 14.96 g of Meldrum's acid, 0.61 g of 4-dimethylaminopyridine (DMAP), 21.40 g of N,N-dicyclohexylcarbodiimide (DCC) and 200 mL of dichloromethane at room temperature in turn, the mixture was cooled to 0° C. and stirred for 12 hours. The mixture was filtered to remove the precipitated solid, the filtrate was concentrated to give a light-yellow oil. To the above oil was added 95 mL of t-butanol, the mixture was heated to 82° C. under nitrogen. The raw materials were consumed monitored by TLC, the reaction liquid was distilled under reduced pressure to remove t-butanol, to the residue was added 100 mL of dichloromethane, the resulting mixture was washed with water and saturated sodium chloride aqueous solution respectively, the organic layers were combined and concentrated in vacuo to give t-butyl 4-([1,1'-biphenyl]-4-yl)-3-oxobutyrate 24.89 g, the yield was 85%. $^1$H NMR (600 MHz, CDCl$_3$) δ 7.57 (t, J=6.8 Hz, 4H), 7.43 (t, J=7.4 Hz, 2H), 7.38-7.32 (m, 1H), 7.31-7.25 (m, 2H), 3.87 (s, 2H), 3.41 (s, 2H), 1.47 (s, 9H). ESI-MS (m/z): 311.4 ([M+H]+).

Example 5-b: Preparation of (3R)-4-benzyl-1-t-butyl-2-(2-([1,1'-biphenyl]-4-yl)acetyl)-3-methylsuccinate

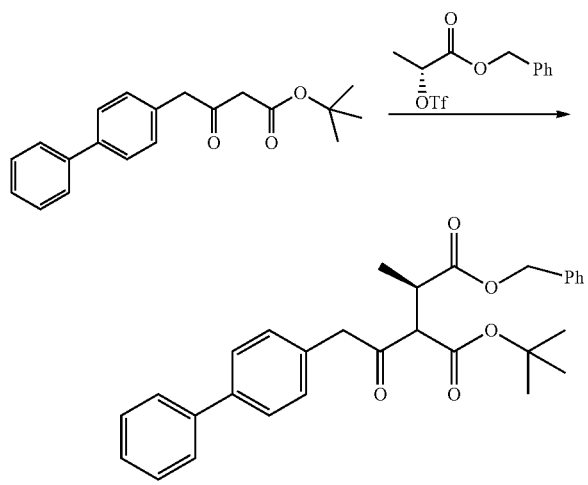

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of t-butyl 4-([1,1'-biphenyl]-4-yl)-3-oxobutyrate in 100 mL of tetrahydrofuran was added dropwise slowly under nitrogen. After the addition, the reaction liquid was heated to a temperature of 20° C. to 30° C. and stirred for additional 30 min. The reaction liquid was cooled to 0° C., and a solution of 33.37 g of (R)-benzyl-2-(triflate)propionate in 100 mL of tetrahydrofuran was added dropwise slowly, after the addition, the reaction liquid was heated to a temperature of 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, then concentrated in vacuo to give an oil (3R)-4-benzyl-1-t-butyl-2-(2-([1,1'-biphenyl]-4-yl)acetyl)-3-methylsuccinate 50.60 g, which was used in the next step without further purification.

Example 5-c: Preparation of (R)-benzyl-benzyl-5-([1,1'-biphenyl]-4-yl)-2-methyl-4-oxopentanoate

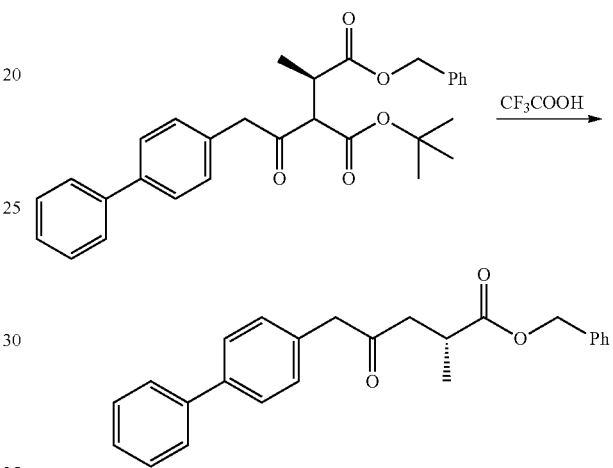

To a 100 mL flask were added 6.00 g of (3R)-4-benzyl-1-t-butyl-2-(2-([1,1'-biphenyl]-4-yl)acetyl)-3-methylsuccinate, 30 mL of dichloromethane (DCM) and 11.01 g of trifluoroacetic acid (CF$_3$COOH), the mixture was heated to 42° C. with stirring and reacted for 22 hours. After the raw materials were consumed completely monitored by HPLC, to the reaction liquid was added 150 mL of 6.5% sodium bicarbonate solution dropwise slowly, and 150 mL of 2 N hydrochloric acid was added to adjust pH to 2-3, and the reaction liquid was extracted with ethyl acetate 3 times, each time with 100 mL. The organic layers were combined and washed 2 times with 200 mL each time of water, then concentrated in vacuo to give an oil (R)-benzyl 5-([1,1'-biphenyl]-4-yl)-2-methyl-4-oxopentanoate 4.10 g, the yield was 86.7%. $^1$H NMR (400 MHz, CDCl$_3$) δ 7.60 (t, J=7.7 Hz, 4H), 7.46 (t, J=7.6 Hz, 2H), 7.40-7.33 (m, 5H), 7.37 (t, J=7.3 Hz, 1H), 7.30 (d, J=8.1 Hz, 2H), 5.22 (s, 2H), 3.78 (s, 2H), 3.04-2.94 (m, 2H), 2.60-2.51 (m, 1H), 1.18 (d, J=6.8 Hz, 3H). ESI-MS (m/z): 373.5 ([M+H]+).

Example 6. Preparation of (R)-5-([1,1'-biphenyl]-4-yl)-N,2-dimethyl-4-oxovaleramide Example 6-a: Preparation of Ethyl 4-([1,1'-biphenyl]-4-yl)-3-oxobutyrate The procedure is the same as the procedure of Example 1-a.

Example 6-b: Preparation of (3R)-ethyl-2-(2-([1,1'-biphenyl]-4-yl)acetyl)-3-methyl-4-methylamino-4-oxobutyrate

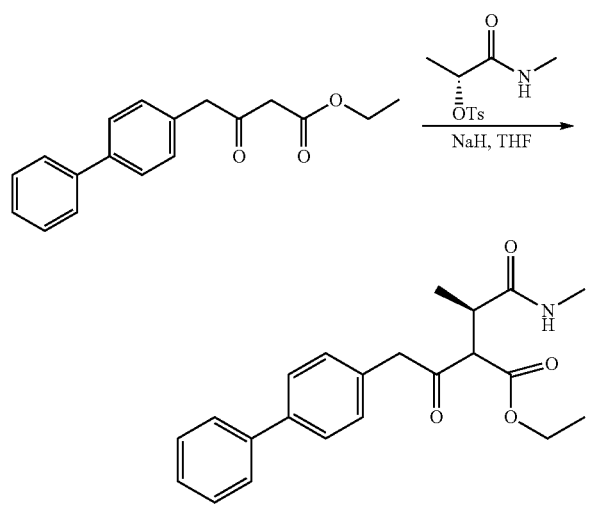

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of ethyl 4-([1,1'-biphenyl]-4-yl)-3-oxobutyrate in 100 mL of tetrahydrofuran (THF) was added dropwise slowly under nitrogen. After the addition, the reaction liquid was heated to a temperature of 20° C. to 30° C. and stirred for additional 30 min. The reaction liquid was cooled to 0° C., and a solution of 31.37 g of (R)-1-methylamino-1-oxopropyl-2-yl-4-methylbenzenesulfonate in 100 mL of tetrahydrofuran (THF) was added dropwise slowly, after the addition, the reaction liquid was heated to a temperature of 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, then concentrated in vacuo to give an oil (3R)-ethyl 2-(2-([1,1'-biphenyl]-4-yl)acetyl)-3-methyl-4-methylamino-4-oxobutyrate 48.60 g, which was used in the next step without further purification.

Example 6-c: Preparation of (R)-5-([1,1'-biphenyl]-4-yl)-N,2-dimethyl-4-oxovaleramide

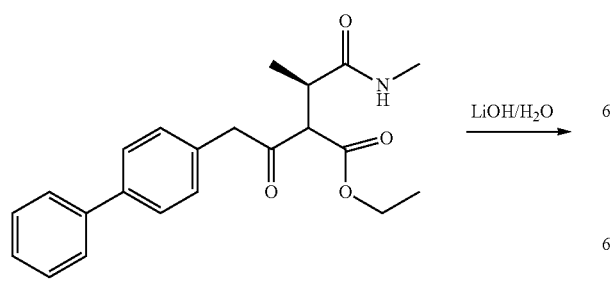

To a 500 mL flask were added 15.00 g of (3R)-ethyl-2-(2-([1,1'-biphenyl]-4-yl)acetyl)-3-methyl-4-methylamino-4-oxobutyrate and 130 mL of tetrahydrofuran (THF), the reaction liquid was cooled to 0° C., a solution of 4.00 g of lithium hydroxide monohydrate (LiOH—H$_2$O) in 130 mL of water was added dropwise slowly. After the addition, the reaction liquid was heated to a temperature of 60° C. to 70° C. and stirred for additional 16 hours. After the raw materials were consumed completely monitored by HPLC, the reaction liquid was cooled to a temperature of 20° C. to 30° C., 100 mL of 1 N hydrochloric acid was added to adjust pH to 2-3, and the reaction liquid was extracted with ethyl acetate 3 times, each time with 100 mL. The organic layers were combined and washed with water 2 times, each time with 200 mL, and then concentrated in vacuo to give an oil (R)-5-([1,1'-biphenyl]-4-yl)-N,2-dimethyl-4-oxovaleramide 10.43 g, the yield is 86.5%. $^1$H NMR (600 MHz, DMSO-d$_6$) δ 12.16 (s, 1H), 7.66 (d, J=7.3 Hz, 2H), 7.61 (d, J=8.1 Hz, 2H), 7.46 (t, J=7.7 Hz, 2H), 7.36 (t, J=7.4 Hz, 1H), 7.28 (d, J=8.1 Hz, 2H), 3.82 (s, 2H), 3.05 (s, 3H), 2.88 (dd, J=17.7, 8.1 Hz, 1H), 2.76-2.69 (m, 1H), 2.61 (dd, J=17.7, 5.4 Hz, 1H), 1.05 (dd, J=16.4, 7.1 Hz, 3H). ESI-MS (m/z): 296.3 ([M+H]+).

Example 7. Preparation of (R)-5-([1,1'-biphenyl]-4-yl)-N-t-butyl-2-methyl-4-oxovaleramide

Example 7-a: Preparation of Ethyl 4-([1,1'-biphenyl]-4-yl)-3-oxobutyrate

The procedure is the same as the procedure of Example 1-a.

Example 7-b: Preparation of (3R)-ethyl-2-(2-([1,1'-biphenyl]-4-yl)acetyl)-3-methyl-4-t-butylamino-4-oxobutyrate

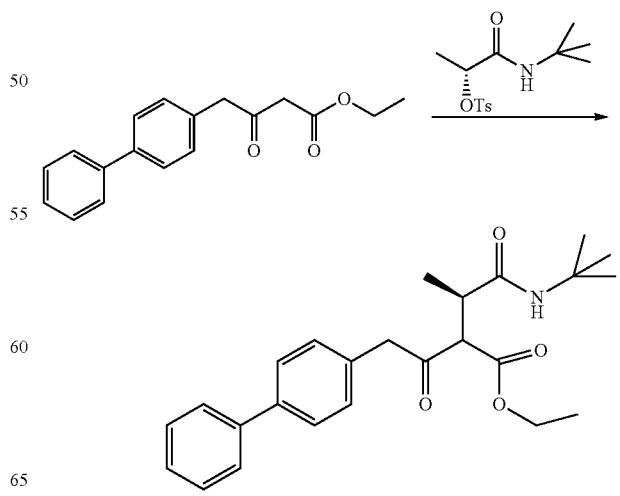

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of ethyl 4-([1,1'-biphenyl]-4-yl)-3-oxobutyrate in 100 mL of tetrahydrofuran (THF) was added dropwise slowly under nitrogen. After the addition, the reaction liquid was heated to a temperature of 20° C. to 30° C. and stirred for additional 30 min. The reaction liquid was cooled to 0° C., and a solution of 31.37 g of (R)-1-t-butylamino-1-oxopropyl-2-yl-4-methylbenzenesulfonate in 100 mL of tetrahydrofuran (THF) was added dropwise slowly, after the addition, the reaction liquid was heated to a temperature of 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed with water 2 times, each time with 200 mL, and then concentrated in vacuo to give an oil (3R)-ethyl-2-(2-([1,1'-biphenyl]-4-yl)acetyl)-3-methyl-4-t-butylamino-4-oxobutyrate 48.60 g, which was used in the next step without further purification.

Example 7-c: Preparation of (R)-5-([1,1'-biphenyl]-4-yl)-N-t-butyl-2-methyl-4-oxovaleramide

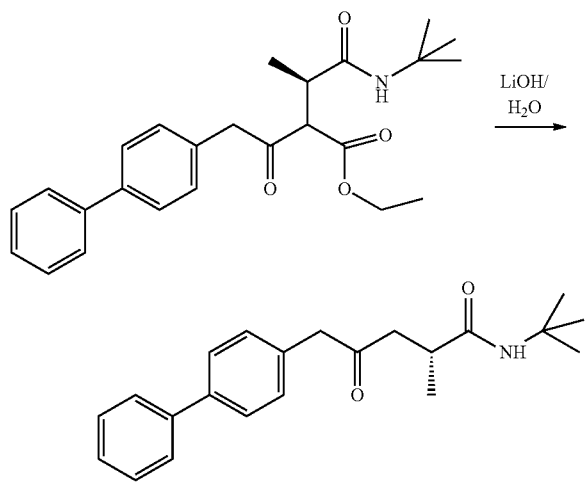

To a 500 mL flask were added 15.00 g of (3R)-ethyl-2-(2-([1,1'-biphenyl]-4-yl)acetyl)-3-methyl-4-t-butylamino-4-oxobutyrate and 130 mL of tetrahydrofuran (THF), the reaction liquid was cooled to 0° C., a solution of 4.00 g of lithium hydroxide monohydrate (LiOH—H₂O) in 130 mL of water was added dropwise slowly. After the addition, the reaction liquid was heated to a temperature of 60° C. to 70° C. and stirred for additional 16 hours. After the raw materials were consumed completely monitored by HPLC, the reaction liquid was cooled to a temperature of 20° C. to 30° C., 100 mL of 1 N hydrochloric acid was added to adjust pH to 2-3, and the reaction liquid was extracted with ethyl acetate 3 times, each time with 100 mL. The organic layers were combined and washed 2 times with 200 mL each time of water, then concentrated to give an oil (R)-5-([1,1'-biphenyl]-4-yl)-N-t-butyl-2-methyl-4-oxovaleramide 10.05 g, the yield was 81.3%. ¹H NMR (600 MHz, DMSO-d₆) δ 12.16 (s, 1H), 7.66 (d, J=7.3 Hz, 2H), 7.61 (d, J=8.1 Hz, 2H), 7.46 (t, J=7.7 Hz, 2H), 7.36 (t, J=7.4 Hz, 1H), 7.28 (d, J=8.1 Hz, 2H), 3.82 (s, 2H), 2.88 (dd, J=17.7, 8.1 Hz, 1H), 2.76-2.69 (m, 1H), 2.61 (dd, J=17.7, 5.4 Hz, 1H), 1.39 (s, 9H), 1.05 (dd, J=16.4, 7.1 Hz, 3H). ESI-MS (m/z): 338.4 ([M+H]+).

Example 8. Preparation of (R)-1-([1,1'-biphenyl]-4-yl)-4-methyl-5-(triphenylmethoxy)-2-pentanone Example 8-a: Preparation of Ethyl 4-([1,1'-biphenyl]-4-yl)-3-oxobutyrate The procedure is the same as the procedure of Example 1-a.

Example 8-b: Preparation of Ethyl 4-([1,1'-biphenyl]-4-yl)-3-oxo-2-((R)-1-(triphenylmethoxy)propan-2-yl)-butyrate

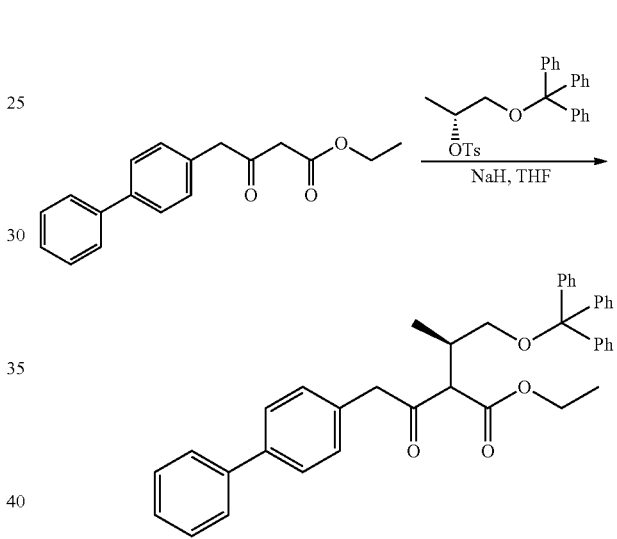

To a 500 mL flask were added 5.31 g of sodium hydride (NaH) and 100 mL of dried toluene, the flask was degassed and filled with nitrogen 3 times. The reaction liquid was cooled to 0° C., a solution of 25.00 g of ethyl 4-([1,1'-biphenyl]-4-yl)-3-oxobutyrate in 100 mL of toluene was added dropwise slowly under nitrogen. After the addition, the reaction liquid was heated to a temperature of 20° C. to 30° C. and stirred for additional 30 min. The reaction liquid was cooled to 0° C., and a solution of 31.37 g of (R)-1-triphenylmethoxyprop-2-yl-4-methylbenzenesulfonate in 100 mL of tetrahydrofuran (THF) was added dropwise slowly, after the addition, the reaction liquid was heated to a temperature of 60° C. to 70° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed with water 2 times, each time with 200 mL, and then concentrated in vacuo to give an oil ethyl 4-([1,1'-biphenyl]-4-yl)-3-oxo-2-((R)-1-(triphenylmethoxy)propan-2-yl)-butyrate 46.60 g, which was used in the next step without further purification.

Example 8-c: Preparation of (R)-1-([1,1'-biphenyl]-4-yl)-4-methyl-5-(triphenylmethoxy)-2-pentanone

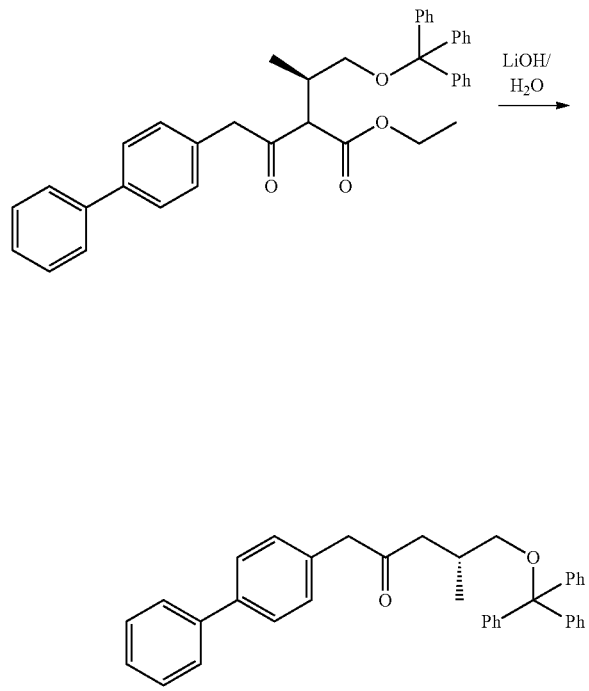 [SMILES: CCOC(=O)C(C(=O)Cc1ccc(-c2ccccc2)cc1)[C@@H](C)COC(c1ccccc1)(c1ccccc1)c1ccccc1 ; C[C@@H](COC(c1ccccc1)(c1ccccc1)c1ccccc1)CC(=O)Cc1ccc(-c2ccccc2)cc1]

To a 500 mL flask were added 15.00 g of ethyl 4-([1,1'-biphenyl]-4-yl)-3-oxo-2-((R)-1-(triphenylmethoxy)propan-2-yl)-butyrate and 130 mL of tetrahydrofuran (THF), the reaction liquid was cooled to 0° C., a solution of 4.00 g of lithium hydroxide monohydrate (LiOH—H$_2$O) in 130 mL of water was added dropwise slowly. After the addition, the reaction liquid was heated to a temperature of 60° C. to 70° C. and stirred for additional 16 hours. After the raw materials were consumed completely monitored by HPLC, the reaction liquid was cooled to a temperature of 20° C. to 30° C., 100 mL of 1 N hydrochloric acid was added to adjust pH to 2-3, and the reaction liquid was extracted with ethyl acetate 3 times, each time with 100 mL. The organic layers were combined and washed with water 2 times, each time with 200 mL, and then concentrated in vacuo to give an oil (R)-1-([1,1'-biphenyl]-4-yl)-4-methyl-5-(triphenylmethoxy)-2-pentanone 11.24 g, the yield was 85.6%. $^1$H NMR (400 MHz, CDCl$_3$) δ 7.60 (t, J=7.7 Hz, 4H), 7.46 (t, J=7.6 Hz, 2H), 7.40-7.33 (m, 5H), 7.38 (m, 15H),7.37 (t, J=7.3 Hz, 1H), 7.30 (d, J=8.1 Hz, 2H), 3.71 (s, 2H), 3.21 (d, J=6.8 Hz, 2H),3.04-2.94 (m, 2H), 2.60-2.51 (m, 1H), 1.18 (d, J=6.8 Hz, 3H). ESI-MS (m/z): 511.6 ([M+H]+).

Example 9. Preparation of (R)-1-([1,1'-biphenyl]-4-yl)-4-methyl-5-(triethylsilyloxy)-2-pentanone

Example 9-a: Preparation of Ethyl 4-([1,1'-biphenyl]-4-yl)-3-oxobutyrate

The procedure is the same as the procedure of Example 1-a.

Example 9-b: Preparation of Ethyl 4-([1,1'-biphenyl]-4-yl)-3-oxo-2-((R)-1-(triethylsilyloxy)prop-2-yl)-butyrate

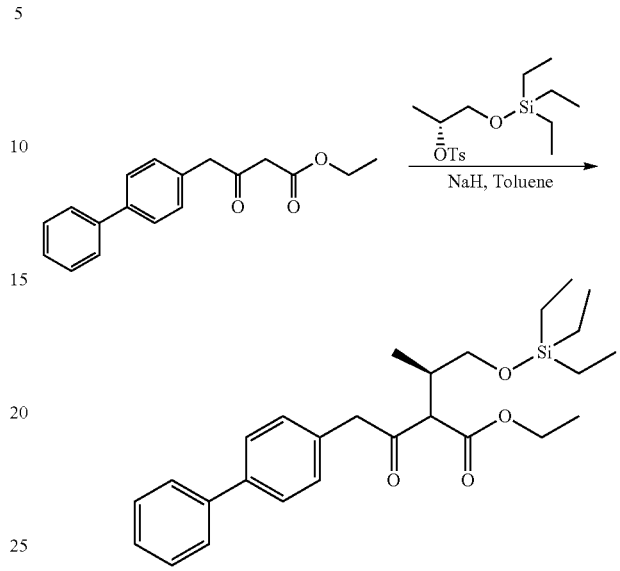

To a 500 mL flask were added 5.31 g of sodium hydride (NaH) and 100 mL of dried toluene, the flask was degassed and filled with nitrogen 3 times. The reaction liquid was cooled to 0° C., a solution of 25.00 g of ethyl 4-([1,1'-biphenyl]-4-yl)-3-oxobutyrate in 100 mL of toluene was added dropwise slowly under nitrogen. After the addition, the reaction liquid was heated to a temperature of 20° C. to 30° C. and stirred for additional 30 min. The reaction liquid was cooled to 0° C., and a solution of 31.37 g of (R)-1-triethylsilyloxyprop-2-yl-4-methylbenzenesulfonate in 100 mL of toluene was added dropwise slowly, after the addition, the reaction liquid was heated to a temperature of 60° C. to 70° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed with water 2 times, each time with 200 mL, and then concentrated in vacuo to give an oil ethyl 4-([1,1'-biphenyl]-4-yl)-3-oxo-2-((R)-1-(triethylsilyloxy)prop-2-yl)-butyrate 44.50 g, which was used in the next step without further purification.

Example 9-c: Preparation of (R)-1-([1,1'-biphenyl]-4-yl)-4-methyl-5-(triethylsilyloxy)-2-pentanone

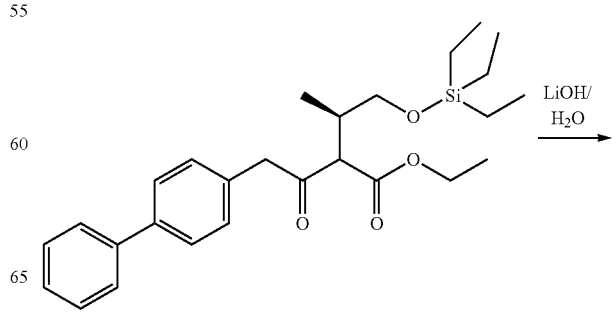

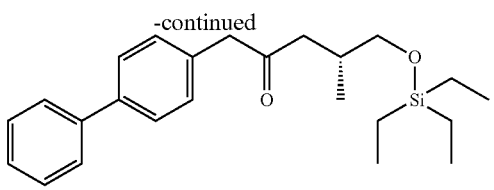

To a 500 mL flask were added 15.00 g of ethyl 4-([1,1'-biphenyl]-4-yl)-3-oxo-2-((R)-1-(triethylsilyloxy)prop-2-yl)-butyrate and 130 mL of tetrahydrofuran (THF), the reaction liquid was cooled to 0° C., a solution of 4.00 g of lithium hydroxide monohydrate (LiOH—H$_2$O) in 130 mL of water was added dropwise slowly. After the addition, the reaction liquid was heated to a temperature of 60° C. to 70° C. and stirred for additional 16 hours. After the raw materials were consumed completely monitored by HPLC, the reaction liquid was cooled to a temperature of 20° C. to 30° C., 100 mL of 1 N hydrochloric acid was added to adjust pH to 2-3, and the reaction liquid was extracted with ethyl acetate 3 times, each time with 100 mL. The organic layers were combined and washed with water 2 times, each time with 200 mL, and then concentrated in vacuo to give an oil (R)-1-([1,1'-biphenyl]-4-yl)-4-methyl-5-(triethylsilyloxy)-2-pentanone 10.97 g, the yield was 86.9%. $^1$H NMR (400 MHz, CDCl$_3$) δ 7.60 (t, J=7.7 Hz, 4H), 7.46 (t, J=7.6 Hz, 2H), 7.40-7.33 (m, 5H), 7.37 (t, J=7.3 Hz, 1H), 7.30 (d, J=8.1 Hz, 2H), 3.71 (s, 2H), 3.63 (m, 2H), 3.04-2.94 (m, 2H), 2.60-2.51 (m, 1H),1.36 (m, 6H), 1.18 (m, 12H). ESI-MS (m/z): 383.6 ([M+H]+).

Example 10. Preparation of (R)-5-([4-iodophenyl])-2-methyl-4-oxopentanoic acid

Example 10-a: Preparation of Ethyl 4-([4-iodophenyl]-4-yl)-3-oxobutyrate

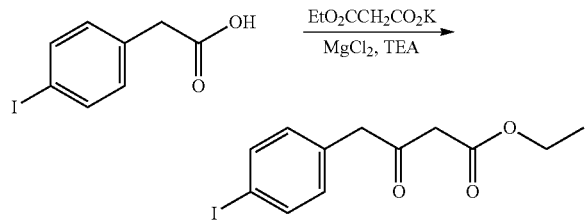

To a 500 mL three neck flask A were added 200 mL of ethyl acetate and 28.64 g of N,N'-carbonyldiimidazole at room temperature, and 25.00 g of 4-iodophenyl acetic acid was added in portions to flask A, the generation rate of gas was controlled. After the addition, the reaction liquid was heated to 45° C. and reacted for 3 hours, and then cooled to a temperature of 20° C. to 30° C., the flask was evacuated for pressure reduction for 1 hour, and ready for use. To a 1 L flask B were added 280 mL of ethyl acetate, 28.06 g of EtO$_2$CCH$_2$COOK and 15.70 g of magnesium chloride (MgCl$_2$) at room temperature, the temperature was controlled at 20° C. to 30° C., and then 19.07 g of triethylamine (TEA) was added dropwise slowly. After the addition, the mixture was further stirred for 1 hour. To flask B was added the materials in flask A at room temperature, the mixture was heated to 45° C. and reacted for 16 hours. The reaction liquid was cooled to a temperature of 20° C. to 30° C., and 180 mL of 4 N hydrochloric acid solution was added, and the mixture was partitioned, the organic layer was washed three times with 250 mL of 6.5% sodium bicarbonate aqueous solution each time, the organic layers were combined, the solvent was then stripped off in vacuo at 45° C. to give a yellow brown oil. To the obtained oil was added 150 mL of n-hexane, the mixture was stirred at 20 to 30° C. for 18 hours and filtered, the filter cake was washed with n-hexane and dried at a temperature of 40° C. to 50° C. in vacuo for 5 hours to give ethyl 4-([4-iodophenyl]-4-yl)-3-oxobutyrate 27.4 g, the yield was 86.5%. 1H NMR (600 MHz, CDCl$_3$) δ, 7.47 (t, J=7.7 Hz, 2H), 7.33-7.28 (m, 2H), 4.25-4.18 (m, 2H), 3.90 (s, 2H), 3.52 (s, 2H), 1.30 (t, J=7.1 Hz, 3H). ESI-MS (m/z): 333.1 ([M+H]+).

Example 10-b: Preparation of (3R)-1-ethyl-4-methyl 2-(2-([4-iodophenyl])acetyl)-3-methylsuccinate

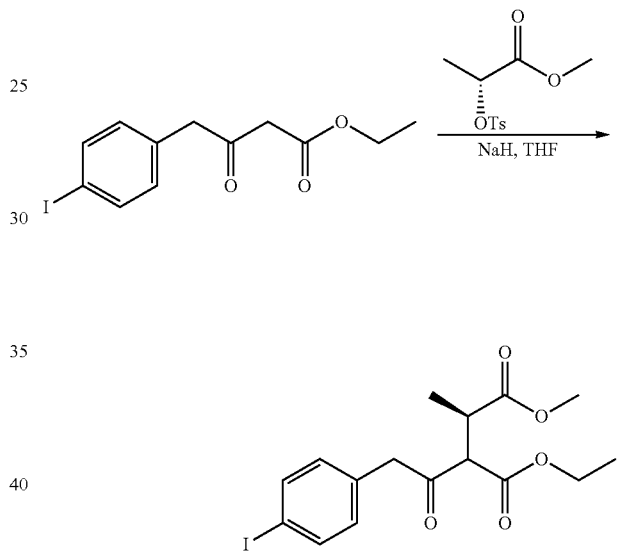

To a 500 mL flask were added 5.31 g of sodium hydride (NaH) and 100 mL dried tetrahydrofuran (THF), the flask was degassed and filled with nitrogen 3 times. The reaction liquid was cooled to 0° C., a solution of 25.00 g of ethyl 4-([4-iodophenyl]-4-yl)-3-oxobutyrate in 100 mL of tetrahydrofuran (THF) was added dropwise slowly under nitrogen. After the addition, the reaction liquid was heated to a temperature of 20° C. to 30° C. and stirred for additional 30 min. The reaction liquid was cooled to 0° C., and a solution of 31.37 g of (R)-methyl 2-(4-methylbenzenesulfonate)propionate in 100 mL of tetrahydrofuran (THF) was added dropwise slowly, after the addition, the reaction liquid was heated to a temperature of 20° C. to 30° C. and stirred for 1.5 hours. After the raw materials were consumed completely monitored by HPLC, to the reaction liquid was added 150 mL of 2 N hydrochloric acid to adjust pH to 2-3, and the reaction liquid was extracted with ethyl acetate 3 times, each time with 100 mL. The organic layers were combined and washed 2 times with 200 mL each time of water, then concentrated in vacuo to give an oil (3R)-1-ethyl-4-methyl 2-(2-([4-iodophenyl])acetyl)-3-methylsuccinate 48.60 g, which was used in the next step without further purification.

Example 10-c: Preparation of (R)-5-([4-iodophenyl])-2-methyl-4-oxopentanoic acid

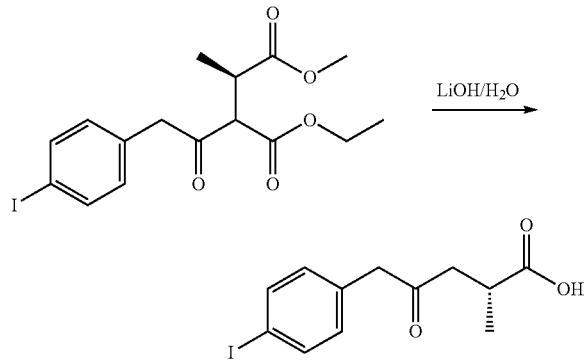

To a 500 mL flask were added 13.00 g of (3R)-1-ethyl-4-methyl 2-(2-([4-iodophenyl])acetyl)-3-methylsuccinate and 130 mL of tetrahydrofuran (THF), the reaction liquid was cooled to 0° C., a solution of 3.71 g of lithium hydroxide monohydrate (LiOH—H$_2$O) in 130 mL of water was added dropwise slowly. After the addition, the reaction liquid was heated to a temperature of 60° C. to 70° C. and stirred for additional 16 hours. After the raw materials were consumed completely monitored by HPLC, the reaction liquid was cooled to a temperature of 20° C. to 30° C., 100 mL of 1 N hydrochloric acid was added to adjust pH to 2-3, and the reaction liquid was extracted with ethyl acetate 2 times, each time with 100 mL. The organic layers were combined and washed 2 times with 200 mL each time of water, then concentrated to give an oil (R)-5-([4-iodophenyl])-2-methyl-4-oxopentanoic acid 8.46 g, the yield was 82.0%. $^1$H NMR (600 MHz, DMSO-d$_6$) δ 12.16 (s, 1H), 7.66 (d, J=7.3 Hz, 2H), 7.28 (d, J=8.1 Hz, 2H), 3.82 (s, 2H), 2.88 (dd, J=17.7, 8.1 Hz, 1H), 2.76-2.69 (m, 1H), 2.61 (dd, J=17.7, 5.4 Hz, 1H), 1.05 (dd, J=16.4, 7.1 Hz, 3H). ESI-MS (m/z): 333.1 ([M+H]+).

Example 11. Preparation of (R)-5-([1,1'-biphenyl]-4-yl)-2-methyl-4-oxopentanoic Acid Example 11-a: Preparation of Methyl 4-([1,1'-biphenyl]-4-yl)-3-oxobutyrate

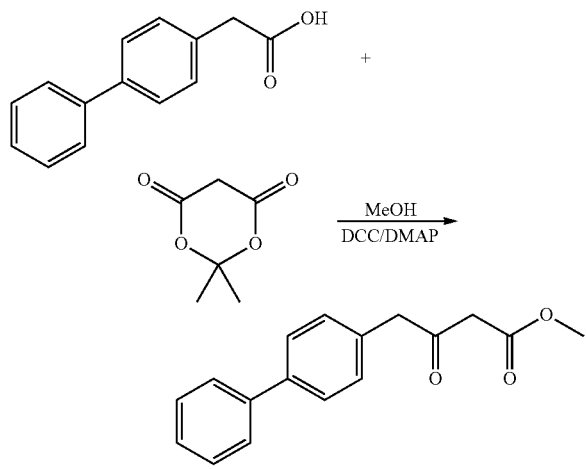

To a 1 L flask were added 20.00 g of 4-biphenylacetic acid, 14.96 g of Meldrum's acid, 0.61 g of 4-dimethylaminopyridine (DMAP), 21.40 g of N,N-dicyclohexylcarbodiimide (DCC) and 200 mL of dichloromethane at room temperature in turn, the mixture was cooled to 0° C. and stirred for 12 hours and filtered to remove precipitated solid, the filtrate was concentrated to give a light yellow oil. To the above oil was added 150 mL of methanol, the mixture was heated to 50° C. under nitrogen, the raw materials were consumed completely monitored by TLC, the reaction liquid was cooled to 0° C. and stirred for 2 hours, and then filtered, the filter cake was dried at 50° C. in vacuo to give a white solid 23.00 g, the yield was 91%. $^1$H NMR (600 MHz, CDCl$_3$) δ 7.59-7.55 (m, 4H), 7.44 (t, J=7.7 Hz, 2H), 7.37-7.31 (m, 1H), 7.30-7.25 (m, 2H), 3.87 (s, 2H), 3.72 (d, J=6.0 Hz, 3H), 3.50 (d, J=10.0 Hz, 2H). ESI-MS (m/z): 269.3 ([M+H]+).

Example 11-b: Preparation of (3R)-dimethyl-2-(2-([1,1'-biphenyl]-4-yl)acetyl)-3-methylsuccinate

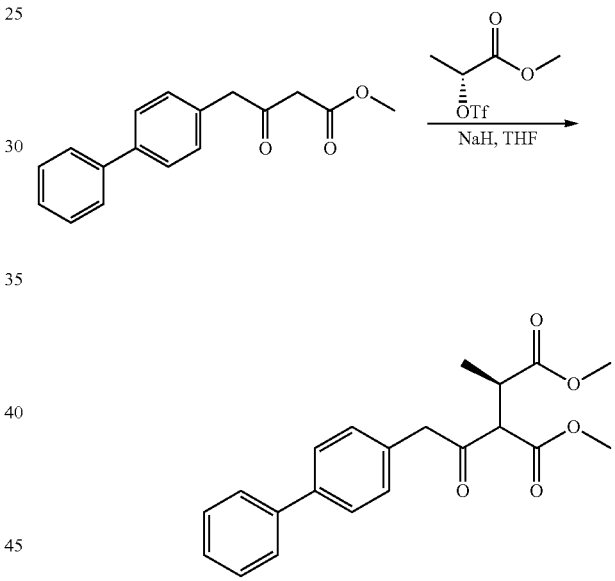

To a 500 mL of flask were added 5.31 g of NaH and 100 mL of dry THF, the mixture was degassed and filled with nitrogen 3 times. The reaction liquid was cooled to 0° C., a solution of 25.00 g of methyl 4-([1,1'-biphenyl]-4-yl)-3-oxobutyrate in 100 mL of THF was added dropwise slowly under nitrogen. After the addition, the reaction liquid was heated to a temperature of 20° C. to 30° C. and stirred for additional 30 min, and then cooled to 0° C., and a solution of 31.37 g of (R)-methyl-2-(triflate)propionate in 100 mL of tetrahydrofuran was added dropwise slowly, after the addition, the reaction liquid was heated to a temperature of 20° C. to 30° C. and stirred for 1.5 hours. After the raw materials were consumed completely monitored by TLC, to the reaction liquid was added 150 mL of 2 N hydrochloric acid to adjust pH to 2-3, and the reaction liquid was extracted with ethyl acetate 3 times. The organic layers were combined and washed with water, and then concentrated in vacuo to give an oil 48.60 g, which was used in the next step without further purification.

Example 11-c: Preparation of (R)-5-([1,1'-biphenyl]-4-yl)-2-methyl-4-oxopentanoic acid

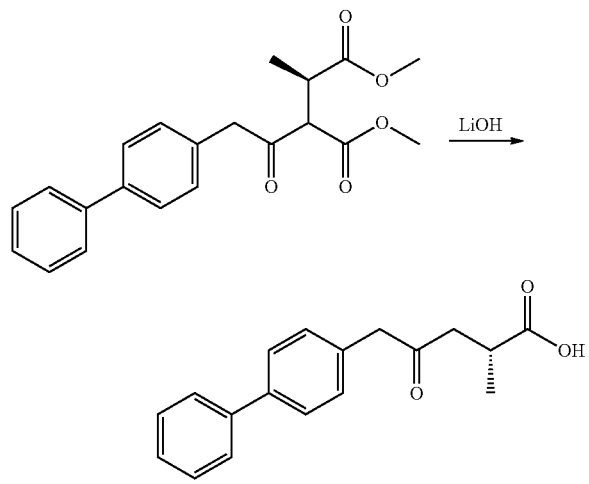

To a 500 mL flask were added 15.00 g of (3R)-dimethyl-2-(2-([1,1'-biphenyl]-4-yl)acetyl)-3-methylsuccinate, 130 mL of tetrahydrofuran (THF) and 3.71 g of lithium hydroxide. The reaction liquid was heated to a temperature of 60° C. to 70° C. and stirred for additional 16 hours. After the raw materials were consumed completely monitored by TLC, the reaction liquid was cooled to a temperature of 20° C. to 30° C., 100 mL of 1 N hydrochloric acid was added to adjust pH to 2-3, and the reaction liquid was extracted with ethyl acetate 3 times. The organic layers were combined and washed with water, and then concentrated in vacuo to give an oil, the oil was recrystallized from ethyl acetate and n-hexane (volume rate was 1:1) to give a white solid 7.76 g, the yield was 65%. $^1$H NMR (600 MHz, DMSO-d$_6$) δ 12.16 (s, 1H), 7.66 (d, J=7.3 Hz, 2H), 7.61 (d, J=8.1 Hz, 2H), 7.46 (t, J=7.7 Hz, 2H), 7.36 (t, J=7.4 Hz, 1H), 7.28 (d, J=8.1 Hz, 2H), 3.82 (s, 2H), 2.88 (dd, J=17.7, 8.1 Hz, 1H), 2.76-2.69 (m, 1H), 2.61 (dd, J=17.7, 5.4 Hz, 1H), 1.05 (dd, J=16.4, 7.1 Hz, 3H). ESI-MS (m/z): 283.3 ([M+H]+).

First Method of Preparing Sacubitril

Example 12. Preparation of Sacubitril Example 12-a: Preparation of (2R,4S)-5-([1,1'-biphenyl]-4-yl)-4-amino-2-methylperntanoic Acid

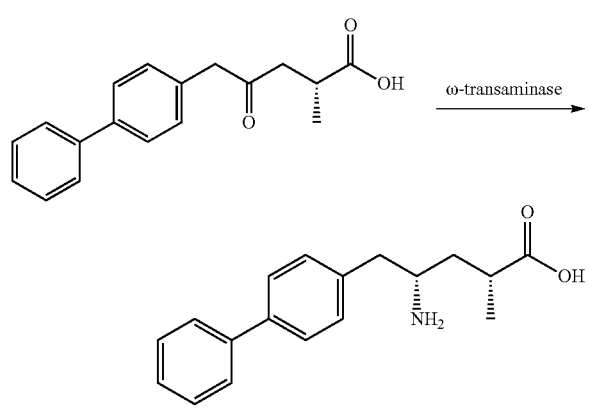

100 g of isopropylamine was dissolved in 100 mL of water, the mixture was adjusted with hydrochloric acid aqueous solution to pH 7.5 to 8.0, and then 250 mL of dimethyl sulfoxide (DMSO) was added. The mixture was diluted with 0.1 M hydrochloric acid tri(hydroxymethyl)aminomethane-hydrochloric acid (Tris-hydrochloric acid) buffer to a volume of 1000 mL and heated to 40° C., 10 g of ω-transaminase freeze dry powder and 8.0 g of pyridoxal phosphate (PLP) were added, and then a solution of 100 g of (R)-5-([1,1'-biphenyl]-4-yl)-2-methyl-4-oxopentanoic acid in 250 mL of dimethyl sulfoxide (DMSO) prepared by the method in example 1 was added dropwise, 20% isopropylamine aqueous solution was used to control pH 7.5 to 8.0 in the reaction process, the temperature was maintained at 40° C. to 45° C. for 24 hours during the reaction procedure, the reaction was monitored by TLC until completed. The mixture was filtered to remove solid, and the parent liquid was extracted with ethyl acetate 3 times, the organic layers were combined and concentrated in vacuo to give a light yellow solid 90.2 g, the yield was 90.2%, ee value is 99%. $^1$H NMR (600 MHz, DMSO-d$_6$) δ 8.22 (s, 2H), 7.66 (dd, J=14.2, 7.7 Hz, 4H), 7.47 (t, J=7.7 Hz, 2H), 7.36 (t, J=8.0 Hz, 3H), 3.43 (d, J=5.4 Hz, 1H), 3.05 (dd, J=13.9, 5.7 Hz, 1H), 2.86 (dd, J=13.9, 7.7 Hz, 1H), 2.66 (m, J=13.9, 7.0 Hz, 1H), 1.86 (m, J=14.2, 8.7, 5.5 Hz, 1H), 1.59 (m, J=13.9, 7.7, 5.9 Hz, 1H), 1.07 (d, J=7.0 Hz, 3H). ESI-MS (m/z): 284.3 ([M+H]+).

Example 12-b: Preparation of (2R,4S)-ethyl 5-([1,1'-biphenyl]-4-yl)-4-amino-2-methylpentanoate

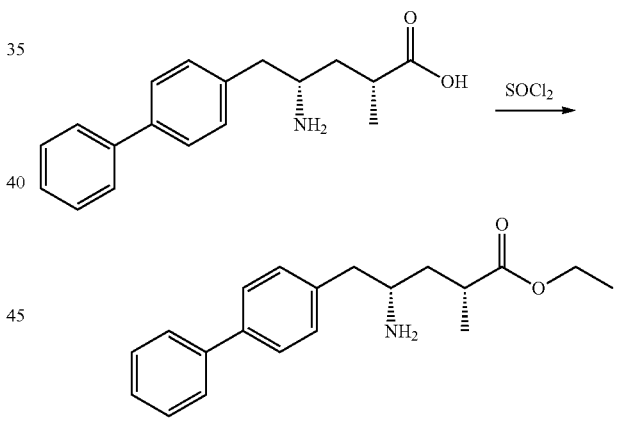

To a 500 mL flask were added 70.00 g of (2R,4S)-5-([1,1'-biphenyl]-4-yl)-4-amino-2-methylpentanoic acid and 350 mL of anhydrous ethanol in turn, the mixture was heated to 40° C. and stirred for dissolution to get a clear solution. To the reaction liquid was added 32.57 g of thionyl chloride dropwise slowly, after the addition, the mixture was heated to 70° C. for reaction. After the raw materials were consumed completely monitored by HPLC, the reaction system was cooled to room temperature slowly and concentrated in vacuo to remove the solvent to give an off-white solid, and to the solid was added 630 mL of ethyl acetate, the resulting mixture was heated to 60° C. and stirred for 2 hours, and then cooled to 25° C. and stirred for additional 2 hours. The mixture was filtered, the filter cake was dried at 50° C. in vacuo to give a white solid 70.77 g, the yield was 92%. $^1$H NMR (600 MHz, CDCl$_3$) δ 8.62 (s, 2H), 7.54 (dd, J=14.1, 7.7 Hz, 4H), 7.41 (t, J=7.6 Hz, 2H), 7.36-7.29 (m, 3H), 4.07

(q, J=7.1 Hz, 2H), 3.67 (s, 1H), 3.40-3.34 (m, 1H), 2.97 (dd, J=24.3, 10.9 Hz, 2H), 2.07-2.00 (m, 1H), 1.90-1.83 (m, 1H), 1.20-1.15 (m, 6H). ESI-MS (m/z): 312.4 ([M+H]+).

Example 12-c: Preparation of Sacubitril

Sacubitril was prepared by the method described in the paragraphs [0038] to [0039] of example 8 of the specification of CN 104557600 A, the yield was 91.8%.

$^1$H NMR (400 MHz, DMSO) δ 7.96 (d, J=8.2 Hz, 1H), 7.62 (d, J=7.4 Hz, 2H), 7.55 (d, J=8.1 Hz, 2H), 7.43 (t, J=7.6 Hz, 2H), 7.33 (t, J=7.3 Hz, 1H), 7.24 (d, J=8.1 Hz, 2H), 4.02-3.86 (m, 3H), 2.74 (dd, J=13.4, 6.3 Hz, 1H), 2.64 (dd, J=13.4, 6.8 Hz, 1H), 2.50-2.44 (m, 1H), 2.26 (dd, J=22.4, 7.3 Hz, 4H), 1.81-1.68 (m, 1H), 1.47-1.36 (m, 1H), 1.10 (t, J=7.1 Hz, 3H), 1.04 (d, J=7.0 Hz, 3H). ESI-MS (m/z): 412.2 ([M+H]+).

Example 13. Preparation of Sacubitril

Example 13-a: Preparation of (2R,4S)-methyl 5-([1,1'-biphenyl]-4-yl)-4-amino-2-methylpentanoate

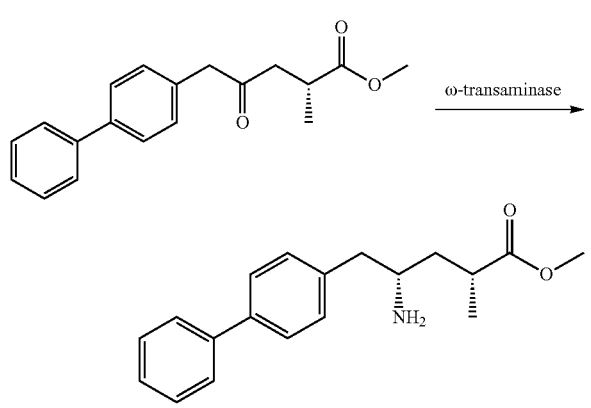

10 g of isopropylamine was dissolved in 10 mL of water, the mixture was adjusted with hydrochloric acid aqueous solution to pH 7.5 to 8.0, and then 25 mL of dimethyl sulfoxide (DMSO) was added. The mixture was diluted with 0.1 M hydrochloric acid tri(hydroxymethyl)aminomethane-hydrochloric acid (Tris-hydrochloric acid) buffer to a volume of 100 mL and heated to 40° C., 1.0 g of ω-transaminase freeze dry powder and 0.8 g of pyridoxal phosphate (PLP) were added, and then a solution of 10 g of (R)-methyl 5-([1,1'-biphenyl]-4-yl)-2-methyl-4-oxopentanoate in 25 mL of dimethyl sulfoxide (DMSO) prepared by the method in example 2 was added dropwise, 20% isopropylamine aqueous solution was used to control pH 7.5 to 8.0 in the reaction process, the temperature was maintained at 40° C. to 45° C. for 24 hours, the reaction was monitored by TLC until completed. The mixture was filtered to remove solid, and the parent liquid was extracted with ethyl acetate 3 times, the organic layers were combined and concentrated in vacuo to give a light yellow solid 8.95 g, the yield was 89.6%, ee value was 98.5%. $^1$H NMR (600 MHz, DMSO-d$_6$) δ 8.22 (s, 2H), 7.65 (dd, J=14.2, 7.7 Hz, 4H), 7.46 (t, J=7.7 Hz, 2H), 7.36 (t, J=8.0 Hz, 3H), 3.68 (s, 3H), 3.43 (d, J=5.4 Hz, 1H), 3.05 (dd, J=13.9, 5.7 Hz, 1H), 2.86 (dd, J=13.9, 7.7 Hz, 1H), 2.66 (m, J=13.9, 7.0 Hz, 1H), 1.86 (m, J=14.2, 8.7, 5.5 Hz, 1H), 1.59 (m, J=13.9, 7.7, 5.9 Hz, 1H), 1.07 (d, J=7.0 Hz, 3H). ESI-MS (m/z): 311.3 ([M+H]+).

Example 13-b: Preparation of (2R,4S)-5-([1,1'-biphenyl]-4-yl)-4-amino-2-methylpentanoic Acid

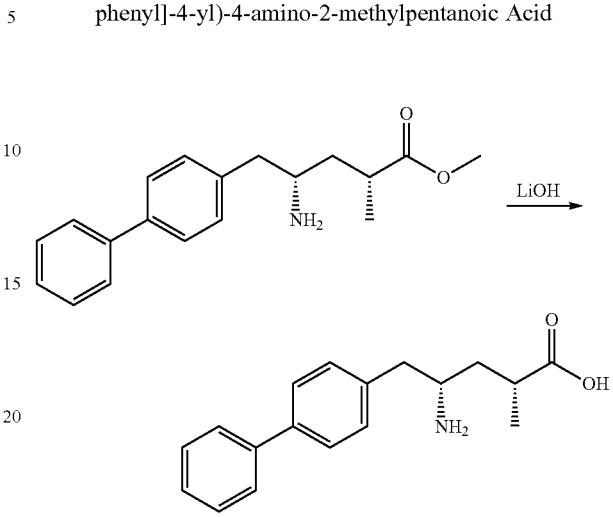

To a 250 mL flask were added 10 g of (2R,4S)-methyl 5-([1,1'-biphenyl]-4-yl)-4-amino-2-methylpentanoate, 50 mL of tetrahydrofuran, 50 mL of methanol and 2.41 g of lithium hydroxide in turn, the mixture was stirred at a temperature of 20° C. to 40° C. for 12 hours, the reaction was monitored by TLC until completed. The solvent was evaporated in vacuo, to the residue were added 100 mL of water and 100 mL of ethyl acetate, and the mixture was stirred for 10 min, the organic layer was separated and concentrated in vacuo to give a light yellow solid 8.19 g, the yield was 86%. $^1$H NMR (600 MHz, DMSO-d$_6$) δ 8.22 (s, 2H), 7.66 (dd, J=14.2, 7.7 Hz, 4H), 7.47 (t, J=7.7 Hz, 2H), 7.36 (t, J=8.0 Hz, 3H), 3.43 (d, J=5.4 Hz, 1H), 3.05 (dd, J=13.9, 5.7 Hz, 1H), 2.86 (dd, J=13.9, 7.7 Hz, 1H), 2.66 (m, J=13.9, 7.0 Hz, 1H), 1.86 (m, J=14.2, 8.7, 5.5 Hz, 1H), 1.59 (m, J=13.9, 7.7, 5.9 Hz, 1H), 1.07 (d, J=7.0 Hz, 3H). ESI-MS (m/z): 284.3 ([M+H]+).

Example 13-c: Preparation of (2R,4S)-ethyl 5-([1,1'-biphenyl]-4-yl)-4-amino-2-methylpentanoate The procedure is the same as the procedure of Example 12-b.

Example 13-d: Preparation of Sacubitril

The procedure is the same as Example 12-c.

Example 14. Preparation of Sacubitril

Example 14-a: Preparation of (2R,4S)-ethyl 5-([1,1'-biphenyl]-4-yl)-4-amino-2-methylpentanoate

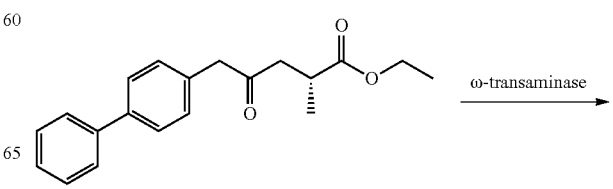

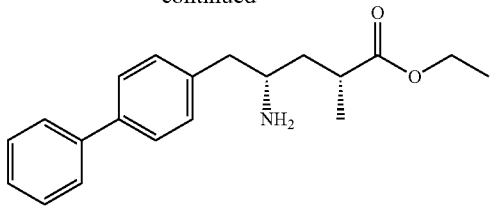

10 g of isopropylamine was dissolved in 10 mL of water, the mixture was adjusted with hydrochloric acid aqueous solution to pH 7.5 to 8.0, and then 25 mL of dimethyl sulfoxide (DMSO) was added. The mixture was diluted with 0.1 M hydrochloric acid tri(hydroxymethyl)aminomethane—hydrochloric acid (Tris-hydrochloric acid) buffer to a volume of 100 mL and heated to 40° C., 1.0 g of ω-transaminase freeze dry powder and 0.8 g of pyridoxal phosphate (PLP) were added, and then a solution of 10 g of (R)-ethyl 5-([1,1'-biphenyl]-4-yl)-2-methyl-4-oxopentanoate in 25 mL of dimethyl sulfoxide (DMSO) prepared by the method in example 3 was added dropwise, 20% isopropylamine aqueous solution was used to control pH 7.5 to 8.0 in the reaction process, the temperature was maintained at 40° C. to 45° C. for 24 hours, the reaction was monitored by TLC until completed. The mixture was filtered to remove solid, and the parent liquid was extracted with ethyl acetate 3 times, the organic layers were combined and concentrated in vacuo to give a light yellow solid 8.80 g, the yield was 88.1%, ee value was 99.0%. $^1$H NMR (600 MHz, CDCl$_3$) δ 8.62 (s, 2H), 7.54 (dd, J=14.1, 7.7 Hz, 4H), 7.41 (t, J=7.6 Hz, 2H), 7.36-7.29 (m, 3H), 4.07 (q, J=7.1 Hz, 2H), 3.67 (s, 1H), 3.40-3.34 (m, 1H), 2.97 (dd, J=24.3, 10.9 Hz, 2H), 2.07-2.00 (m, 1H), 1.90-1.83 (m, 1H), 1.20-1.15 (m, 6H). ESI-MS (m/z): 312.4 ([M+H]+).

Example 14-b: Preparation of Sacubitril

The procedure is the same as the procedure of Example 12-c.

Example 15. Preparation of Sacubitril

Example 15-a: Preparation of (2R,4S)-isopropyl 5-([1,1'-biphenyl]-4-yl)-4-amino-2-methylpentanoate

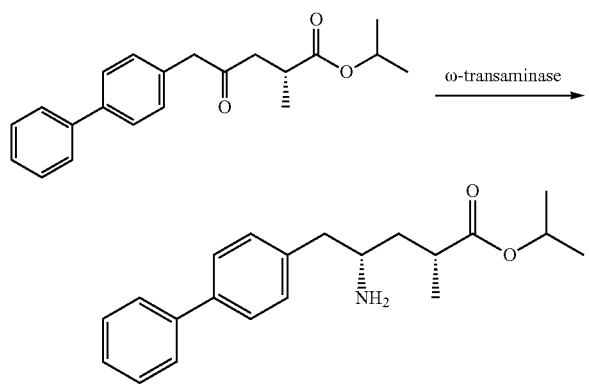

10 g of isopropylamine was dissolved in 10 mL of water, the mixture was adjusted with hydrochloric acid aqueous solution to pH 7.5 to 8.0, and then 25 mL of dimethyl sulfoxide (DMSO) was added. The mixture was diluted with 0.1 M hydrochloric acid tri(hydroxymethyl)aminomethane—hydrochloric acid (Tris-hydrochloric acid) buffer to a volume of 100 mL and heated to 40° C., 1.0 g of ω-transaminase freeze dry powder and 0.8 g of pyridoxal phosphate (PLP) were added, and then a solution of 10 g of (R)-isopropyl 5-([1,1'-biphenyl]-4-yl)-2-methyl-4-oxopentanoate in 25 mL of dimethyl sulfoxide (DMSO) prepared by the method in example 4 was added dropwise, 20% isopropylamine aqueous solution was used to control pH 7.5-8.0 in the reaction process, the temperature was maintained at 40-45° C. for 24 hours, the reaction was monitored by TLC until completed. The mixture was filtered to remove solid, and the parent liquid was extracted with ethyl acetate 3 times, the organic layers were combined and concentrated in vacuo to give a light yellow solid 8.20 g, the yield was 82.1%, ee value was 96.5%. $^1$H NMR (600 MHz, CDCl$_3$) δ 8.62 (s, 2H), 7.54 (dd, J=14.1, 7.7 Hz, 4H), 7.41 (t, J=7.6 Hz, 2H), 7.36-7.29 (m, 3H), 4.93 (m, 1H), 3.67 (s, 1H), 3.40-3.34 (m, 1H), 2.97 (dd, J=24.3, 10.9 Hz, 2H), 2.07-2.00 (m, 1H), 1.90-1.83 (m, 1H), 1.31 (d, J=7.1 Hz, 6H), 1.17 (d, J=6.8 Hz, 3H). ESI-MS (m/z): 326.4 ([M+H]+).

Example 15-b: Preparation of (2R,4S)-5-([1,1'-biphenyl]-4-yl)-4-amino-2-methylpentanoic Acid

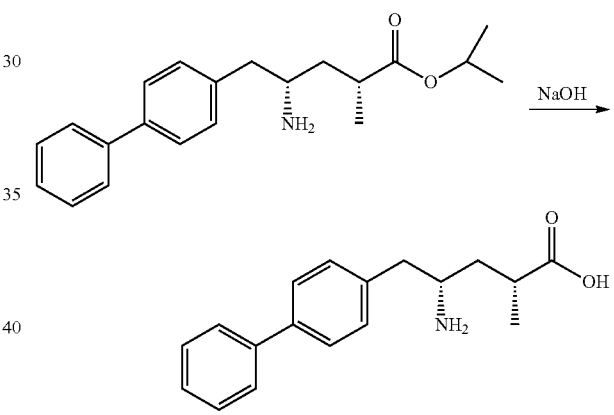

To a 250 mL flask were added 10 g of (2R,4S)-isopropyl 5-([1,1'-biphenyl]-4-yl)-4-amino-2-methylpentanoate, 50 mL of tetrahydrofuran, 50 mL of methanol and 2.65 g of sodium hydroxide in turn, the mixture was stirred at a temperature of 20° C. to 40° C. for 12 hours, the reaction was monitored by TLC until completed. The solvent was evaporated in vacuo, to the residue were added 100 mL of water and 100 mL of ethyl acetate, and the mixture was stirred for 10 min, the organic layer was separated and concentrated in vacuo to give a light yellow solid 7.40 g, the yield was 85%. $^1$H NMR (600 MHz, DMSO-d$_6$) δ 8.22 (s, 2H), 7.66 (dd, J=14.2, 7.7 Hz, 4H), 7.47 (t, J=7.7 Hz, 2H), 7.36 (t, J=8.0 Hz, 3H), 3.43 (d, J=5.4 Hz, 1H), 3.05 (dd, J=13.9, 5.7 Hz, 1H), 2.86 (dd, J=13.9, 7.7 Hz, 1H), 2.66 (m, J=13.9, 7.0 Hz, 1H), 1.86 (m, J=14.2, 8.7, 5.5 Hz, 1H), 1.59 (m, J=13.9, 7.7, 5.9 Hz, 1H), 1.07 (d, J=7.0 Hz, 3H). ESI-MS (m/z): 284.3 ([M+H]+).

Example 15-c: Preparation of (2R,4S)-ethyl 5-([1,1'-biphenyl]-4-yl)-4-amino-2-methylpentanoate The procedure is the same as the procedure of Example 12-b.

Example 15-d: Preparation of Sacubitril

The procedure is the same as the procedure of Example 12-c.

Example 16. Preparation of Sacubitril

Example 16-a: Preparation of (2R,4S)-benzyl 5-([1,1'-biphenyl]-4-yl)-4-amino-2-methylpentanoate

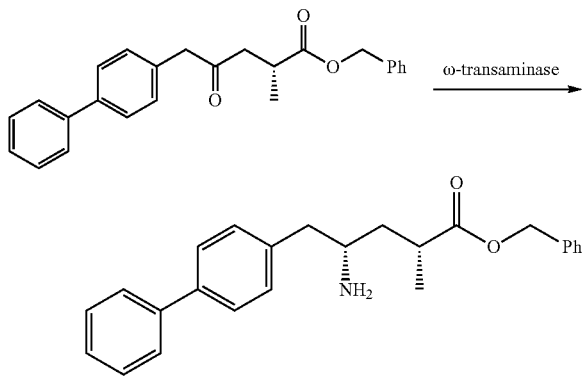

10 g of isopropylamine was dissolved in 10 mL of water, the mixture was adjusted with hydrochloric acid aqueous solution to pH 7.5 to 8.0, and then 25 mL of dimethyl sulfoxide (DMSO) was added. The mixture was diluted with 0.1 M hydrochloric acid tri(hydroxymethyl)aminomethane—hydrochloric acid (Tris-hydrochloric acid) buffer to a volume of 100 mL and heated to 40° C., 1.0 g of ω-transaminase freeze dry powder and 0.8 g of pyridoxal phosphate (PLP) were added, and then a solution of 10 g of (R)-benzyl 5-([1,1'-biphenyl]-4-yl)-2-methyl-4-oxopentanoate in 25 mL of dimethyl sulfoxide (DMSO) prepared by the method in example 5 was added dropwise, 20% isopropylamine aqueous solution was used to control pH 7.5-8.0 in the reaction process, the temperature was maintained at 40-45° C. for 24 hours, the reaction was monitored by TLC until completed. The mixture was filtered to remove solid, and the parent liquid was extracted with ethyl acetate 3 times, the organic layers were combined and concentrated in vacuo to give a light yellow solid 7.90 g, the yield was 79.1%, ee value was 88.0%. $^1$H NMR (600 MHz, CDCl$_3$) δ 8.62 (s, 2H), 7.54 (dd, J=14.1, 7.7 Hz, 4H), 7.41 (t, J=7.6 Hz, 2H), 7.40-7.33 (m, 5H), 7.36-7.29 (m, 3H), 5.22 (s, 2H), 3.67 (s, 1H), 3.40-3.34 (m, 1H), 2.97 (dd, J=24.3, 10.9 Hz, 2H), 2.07-2.00 (m, 1H), 1.90-1.83 (m, 1H), 1.15 (d, J=6.8 Hz, 3H). ESI-MS (m/z): 374.4 ([M+H]+).

Example 16-b: Preparation of (2R,4S)-5-([1,1'-biphenyl]-4-yl)-4-amino-2-methylpentanoic acid

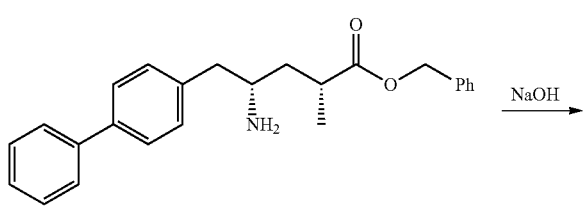

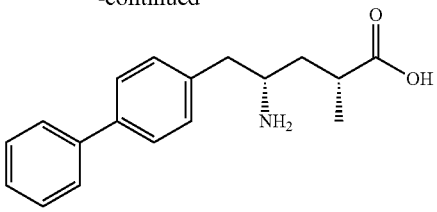

To a 250 mL flask were added 10 g of (2R,4S)-benzyl 5-([1,1'-biphenyl]-4-yl)-4-amino-2-methylpentanoate, 50 mL of tetrahydrofuran, 50 mL of methanol and 2.65 g of sodium hydroxide in turn, the mixture was stirred at the mixture of 20° C. to 40° C. for 12 hours, the reaction was monitored by TLC until completed. The solvent was evaporated in vacuo, to the residue were added 100 mL of water and 100 mL of ethyl acetate, and the mixture was stirred for 10 min, the organic layer was separated and concentrated in vacuo to give a light yellow solid 6.22 g, the yield was 82%. $^1$H NMR (600 MHz, DMSO-d$_6$) δ 8.22 (s, 2H), 7.66 (dd, J=14.2, 7.7 Hz, 4H), 7.47 (t, J=7.7 Hz, 2H), 7.36 (t, J=8.0 Hz, 3H), 3.43 (d, J=5.4 Hz, 1H), 3.05 (dd, J=13.9, 5.7 Hz, 1H), 2.86 (dd, J=13.9, 7.7 Hz, 1H), 2.66 (m, J=13.9, 7.0 Hz, 1H), 1.86 (m, J=14.2, 8.7, 5.5 Hz, 1H), 1.59 (m, J=13.9, 7.7, 5.9 Hz, 1H), 1.07 (d, J=7.0 Hz, 3H). ESI-MS (m/z): 284.3 ([M+H]+).

Example 16-c: Preparation of (2R,4S)-ethyl 5-([1,1'-biphenyl]-4-yl)-4-amino-2-methylpentanoate The procedure is the same as the procedure of Example 12-b.

Example 16-d: Preparation of Sacubitril

The procedure is the same as Example 12-c.

Example 17. Second Method of Preparing Sacubitril

Example 17 Preparation of Sacubitril

Example 17-a: Preparation of (3R,6R,7aR)-7a-([1,1'-biphenyl]-4-ylmethyl)-6-methyl-3-phenyltetrahydropyrrolo-[2,1-b]oxazole-5(6H)-one

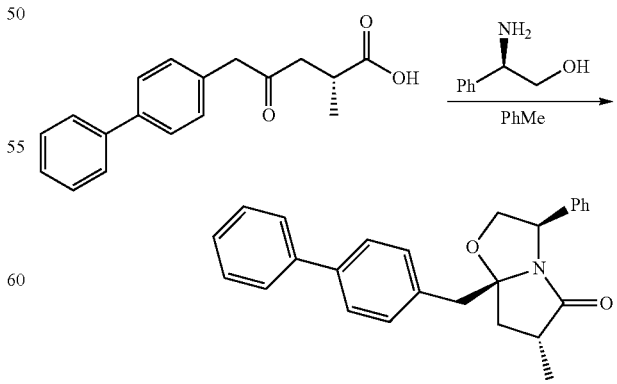

To a 250 mL flask were added 5.90 g of (R)-5-([1,1'-biphenyl]-4-yl)-2-methyl-4-oxopentanoic acid prepared by the method in example 11, 3.42 g of D-phenylglycinol and 60 mL of toluene, the mixture was heated to 125° C. with stirring and reacted for 13 hours. The raw materials were consumed monitored by TLC, the reaction liquid was cooled to a temperature of 20° C. to 30° C. and concentrated in vacuo to give an oil 7.37 g, the yield was 92%. $^1$H NMR (600 MHz, CDCl$_3$) δ 7.61 (dd, J=8.2, 7.1 Hz, 2H), 7.53 (d, J=8.1 Hz, 2H), 7.49-7.40 (m, 6H), 7.39-7.32 (m, 2H), 7.30-7.27 (m, 2H), 5.30 (t, J=7.5 Hz, 1H), 4.73 (t, J=8.4 Hz, 1H), 4.45 (dd, J=8.8, 7.1 Hz, 1H), 3.09 (d, J=13.9 Hz, 1H), 2.96 (d, J=13.9 Hz, 1H), 2.69 (dd, J=12.8, 8.3 Hz, 1H), 2.61-2.51 (m, 1H), 1.74 (t, J=12.1 Hz, 1H), 1.16 (d, J=7.1 Hz, 3H). ESI-MS (m/z): 384.4 ([M+H]+).

Example 17-b: Preparation of (3R,5S)-5-([1,1'-biphenyl-4-yl-methyl)-1-((R)-2-hydroxy-1-phenyl-ethyl)-3-methyl-2-pyrrolidone

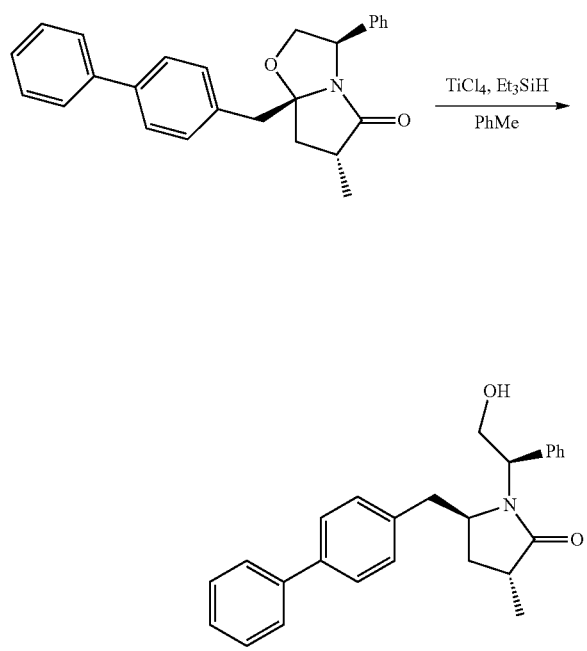

To a 250 mL three neck flask were added 8.02 g of (3R,6R,7aR)-7a-([1,1'-biphenyl]-4-yl-methyl)-6-methyl-3-phenylphenyltetrahydropyrrolo-[2,1-b]oxazole-5(6H)-one and 80 mL of toluene in turn, 7.29 g of triethyl silicane was added to the mixture under nitrogen, the mixture was cooled to −35° C., and 42 mL of titanium tetrachloride in toluene was added dropwise slowly. After the addition, the mixture was stirred for 12 hours. After the raw materials were consumed as monitored by TLC, to the reaction mixture was added 350 mL of 25% ammonium chloride aqueous solution. The organic layer was separated and concentrated in vacuo to give an oil 6.05 g, the yield was 75%. $^1$H NMR (600 MHz, CDCl$_3$) δ 7.56 (d, J=7.4 Hz, 2H), 7.48 (d, J=8.1 Hz, 2H), 7.47-7.40 (m, 4H), 7.40-7.34 (m, 4H), 7.01 (d, J=8.0 Hz, 2H), 4.89 (dd, J=8.0, 4.3 Hz, 1H), 4.19 (dd, J=11.6, 4.3 Hz, 1H), 3.78-3.72 (m, 2H), 3.51 (t, J=6.7 Hz, 1H), 3.13 (dd, J=13.0, 3.9 Hz, 1H), 2.61-2.51 (m, 1H), 2.24 (dd, J=12.8, 11.0 Hz, 1H), 2.19 (ddd, J=13.0, 8.9, 6.9 Hz, 1H), 1.32 (d, J=7.1 Hz, 3H). ESI-MS (m/z): 386.3 ([M+H]+).

Example 17-c: Preparation of (3R,5S)-3-methyl-5-([1,1'-bipheyl]-4-yl-methyl)-2-pyrrolidone

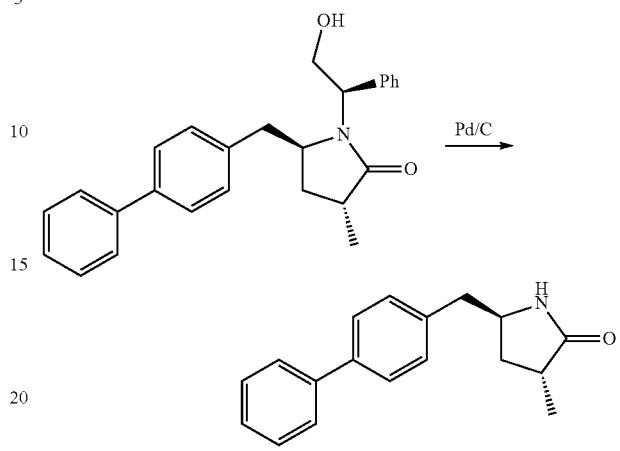

To a 250 mL hydrogenation reaction flask were added 7.00 g of (3R,5S)-5-([1,1'-biphenyl-4-yl-methyl)-1-((R)-2-hydroxy-1-phenylethyl)-3-methyl-2-pyrrolidone, 3.50 g of 10% Pd/C and 70 mL of methanol, the system was degassed and filled with nitrogen 3 times, and the pressure with hydrogen was to 4 Mpa at room temperature, the mixture was heated to 80° C. with stirring and reacted for 24 h, The raw materials were consumed monitored by TLC, the mixture was filtered, and the catalyst was recovered, the filtrate was concentrated in vacuo, the residue was recrystallized from ethyl acetate and n-hexane (volume rate was 1:1) to give a white solid 4.29 g, the yield was 89%. $^1$H NMR (400 MHz, CDCl$_3$) δ 7.63-7.53 (m, 4H), 7.46 (t, J=7.6 Hz, 2H), 7.37 (t, J=7.3 Hz, 1H), 7.30-7.24 (m, 3H), 5.75 (s, 1H), 3.92-3.82 (m, 1H), 2.88 (dd, J=13.4, 5.5 Hz, 1H), 2.77 (dd, J=13.4, 8.4 Hz, 1H), 2.58-2.46 (m, 1H), 2.18 (dt, J=12.5, 7.2 Hz, 1H), 1.96 (dt, J=12.9, 7.8 Hz, 1H), 1.22 (d, J=7.2 Hz, 3H). ESI-MS (m/z): 266.1 ([M+H]+)

Example 17-d: Preparation of (2R,4S)-ethyl 5-([1,1'-biphenyl]-4-yl)-4-amino-2-methylpentanoate Hydrochloride

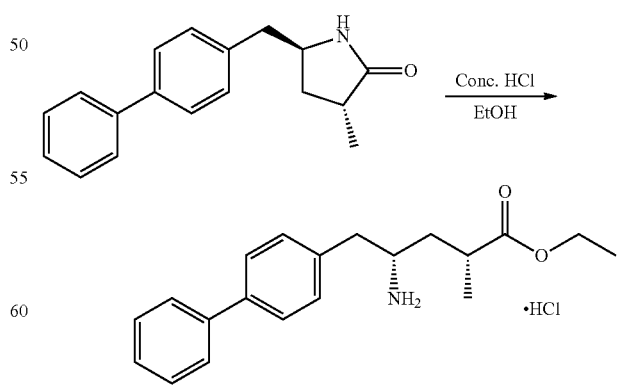

To a 100 mL hydrogenation reaction flask were added 0.65 g of (3R,5S)-3-methyl-5-([1,1'-bipheyl]-4-yl-methyl)-2-pyrrolidone, 20 mL of methanol and 2 mL of concentrated hydrochloric acid, the mixture was heated to a temperature of 70° C. to 85° C. with stirring and reacted for 24 h. The raw materials were consumed monitored by TLC, the mixture was concentrated in vacuo, the residue was recrystallized from ethyl acetate to give a white solid 0.70 g, the yield was 82%. $^1$H NMR (600 MHz, CDCl$_3$) δ 8.62 (s, 3H), 7.54 (dd, J=14.1, 7.7 Hz, 4H), 7.41 (t, J=7.6 Hz, 2H), 7.36-7.29 (m, 3H), 4.07 (q, J=7.1 Hz, 2H), 3.67 (s, 1H), 3.40-3.34 (m, 1H), 2.97 (dd, J=24.3, 10.9 Hz, 2H), 2.07-2.00 (m, 1H), 1.90-1.83 (m, 1H), 1.20-1.15 (m, 6H). ESI-MS (m/z): 312.1 ([M+H]$^+$

Example 17-e: Preparation of Sacubitril

The procedure is the same as the procedure of Example 12-c.

Example 18. Preparation of Sacubitril

Example 18-a: Preparation of (3R,6R,7aR)-7a-([1,1'-biphenyl]-4-yl-methyl)-6-methyl-3-phenyltetrahydropyrrolo-[2,1-b]oxazole-5(6H)-one

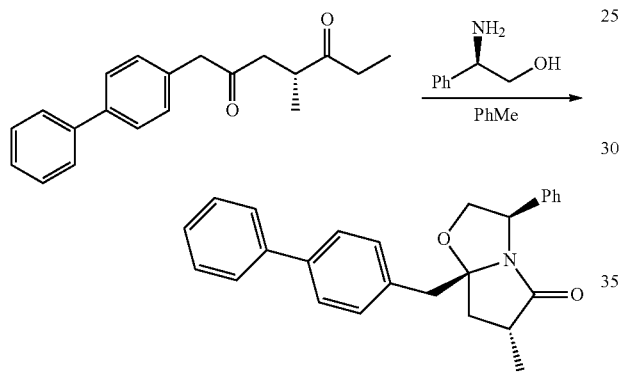

To a 250 mL flask were added 6.50 g of (R)-methyl 5-([1,1'-biphenyl]-4-yl)-2-methyl-4-oxopentanoate prepared by the method in example 2, 3.70 g of D-phenylglycinol and 70 mL of toluene, the mixture was heated to 125° C. with stirring and reacted for 13 hours. The raw materials were consumed monitored by TLC, the reaction liquid was cooled to a temperature of 20° C. to 30° C. and concentrated in vacuo to give an oil 7.23 g, the yield was 86%. $^1$H NMR (600 MHz, CDCl$_3$) δ 7.61 (dd, J=8.2, 7.1 Hz, 2H), 7.53 (d, J=8.1 Hz, 2H), 7.49-7.40 (m, 6H), 7.39-7.32 (m, 2H), 7.30-7.27 (m, 2H), 5.30 (t, J=7.5 Hz, 1H), 4.73 (t, J=8.4 Hz, 1H), 4.45 (dd, J=8.8, 7.1 Hz, 1H), 3.09 (d, J=13.9 Hz, 1H), 2.96 (d, J=13.9 Hz, 1H), 2.69 (dd, J=12.8, 8.3 Hz, 1H), 2.61-2.51 (m, 1H), 1.74 (t, J=12.1 Hz, 1H), 1.16 (d, J=7.1 Hz, 3H). ESI-MS (m/z): 384.4 ([M+H]+).

Example 18-b: Preparation of (3R,5S)-5-([1,1'-biphenyl-4-yl-methyl)-1-((R)-2-hydroxy-1-phenyl-ethyl)-3-methyl-2-pyrrolidone The procedure is the same as the procedure of Example 17-b.

Example 18-c: Preparation of (3R,5S)-3-methyl-5-([1,1'-bipheyl]-4-yl-methyl)-2-pyrrolidone The procedure is the same as the procedure of Example 17-c.

Example 18-d: Preparation of (2R,4S)-ethyl 5-([1,1'-biphenyl]-4-yl)-4-amino-2-methylpentanoate Hydrochloride The procedure is the same as the procedure of Example 17-d.

Example 18-e: Preparation of Sacubitril

The procedure is the same as the procedure of Example 12-c.

As described in the above examples, the synthesis method provided herein can efficiently prepare the compound of Formula (V), and further synthesize sacubitril from the compound of Formula (V). The method disclosed herein has advantages of easily obtained raw materials, simple preparation process, low cost and environment friendly, and so on.

The method of the invention has been described by the preferred embodiment. Related person can clearly realize and apply the techniques disclosed herein by making some changes, appropriate alterations or combinations to the methods without departing from spirit, principles and scope of the present disclosure. Skilled in the art can learn from this article to properly improve the process parameters to implement the preparation method. Of particular note is that all similar substitutions and modifications to the skilled person are obvious, and they are deemed to be included in the present invention.

What is claimed is:
1. A compound of Formula (V),

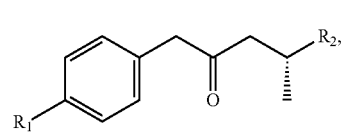

wherein:
R$_1$ is phenyl, methoxy, hydroxy, chloro, bromo, iodo, mesylate, triflate or 4-methylbenzenesulfonate;
R2 is

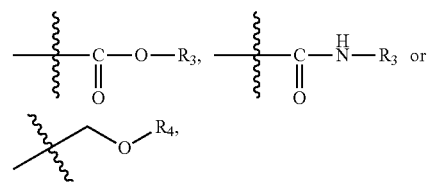

with the proviso that when R$_1$ is phenyl, R2 is not

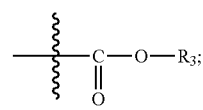

R$_3$ is H, —(C$_1$-C$_4$)alkyl or —(C$_1$-C$_4$)alkyl-aryl; and
R$_4$ is H, —(C$_1$-C$_4$)alkyl, —(C$_3$-C$_6$)heterocyclyl, —(C$_1$-C$_4$)alkyl-aryl, trimethylsilyl, triethylsilyl or t-butyldimethylsilyl.

2. The compound of claim 1, wherein $R_1$ is phenyl.

3. The compound of claim 1, wherein $R_3$ is H, methyl, ethyl, n-propyl, i-propyl, n-butyl, t-butyl, benzyl or substituted benzyl.

4. The compound of claim 1, wherein $R_4$ is H, methyl, ethyl, n-propyl, i-propyl, n-butyl, t-butyl, trimethylsilyl, triethylsilyl, t-butyldimethylsilyl, triphenylmethyl, tetrahydrofuryl, benzyl or substituted benzyl.

5. The compound of claim 1, wherein $R_2$ is —COOH, —COOCH$_3$, —COOCH$_2$CH$_3$, —COOCH(CH$_3$)$_2$, —COOC(CH$_3$)$_3$, —COOCH$_2$Ph, —CH$_2$OH, —CH$_2$OCH$_3$, —CH$_2$OCH$_2$CH$_3$, —CH$_2$OCH(CH$_3$)$_2$, —CH$_2$OC(CH$_3$)$_3$, —CH$_2$OCH$_2$Ph, —CH$_2$OC(Ph)$_3$, —CH$_2$OSi(CH$_3$)$_3$, —CH$_2$OSi(CH$_2$CH$_3$)$_3$, —CH$_2$OSi(CH$_3$)$_2$C(CH$_3$)$_3$, —CONH$_2$, —CONHCH$_3$, —CONHCH$_2$CH$_3$, —CONHCH(CH$_3$)$_2$, —CONHC(CH$_3$)$_3$, —CONHCH$_2$Ph or

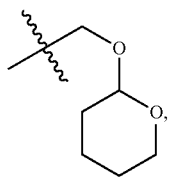 [SMILES: *COC1CCCCO1]

with the proviso that when $R_1$ is phenyl, $R_2$ is —CH$_2$OH, —CH$_2$OCH$_3$, —CH$_2$OCH$_2$CH$_3$, —CH$_2$OCH(CH$_3$)$_2$, —CH$_2$OC(CH$_3$)$_3$, —CH$_2$OCH$_2$Ph, —CH$_2$OC(Ph)$_3$, —CH$_2$OSi(CH$_3$)$_3$, —CH$_2$OSi(CH$_2$CH$_3$)$_3$, —CH$_2$OSi(CH$_3$)$_2$C(CH$_3$)$_3$, —CONH$_2$, —CONHCH$_3$, —CONHCH$_2$CH$_3$, —CONHCH(CH$_3$)$_2$, —CONHC(CH$_3$)$_3$, —CONHCH$_2$Ph or

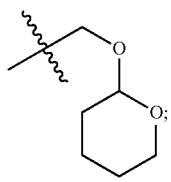 [SMILES: *COC1CCCCO1]

and
wherein each Ph is phenyl.

6. The compound of claim 1 having one of the following structures:

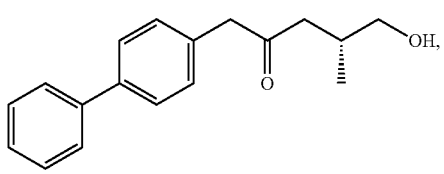 (7)

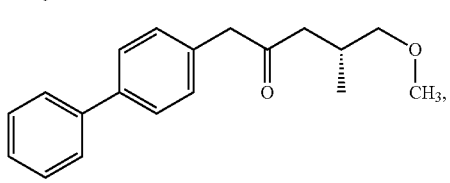 (8)

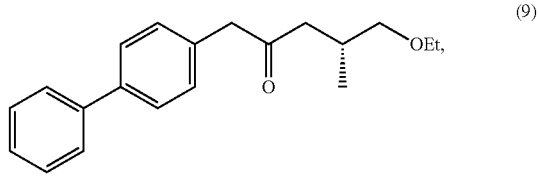 (9)

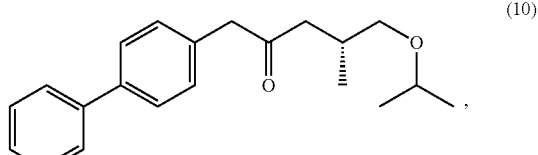 (10)

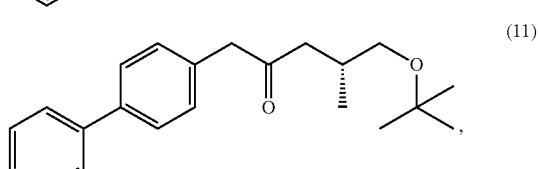 (11)

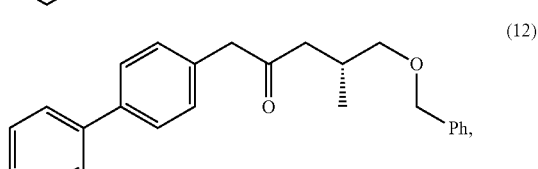 (12)

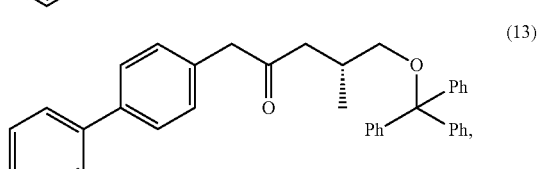 (13)

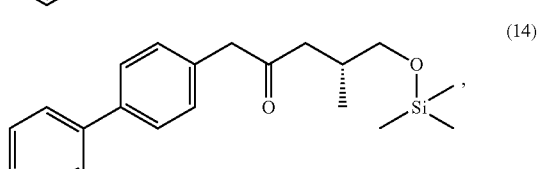 (14)

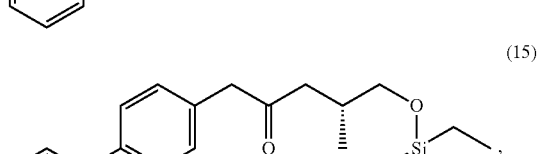 (15)

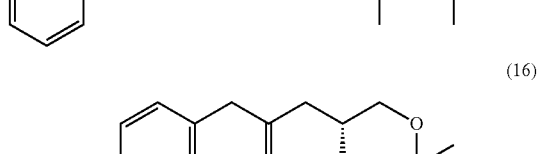 (16)

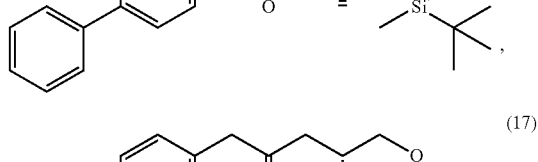 (17)

-continued

(18) 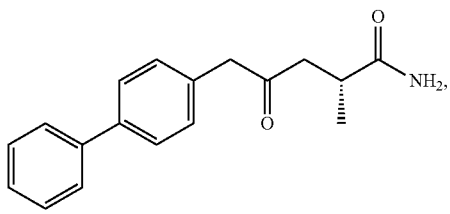

(19) 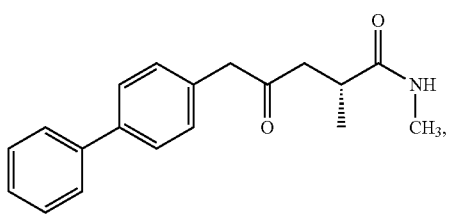

(20) 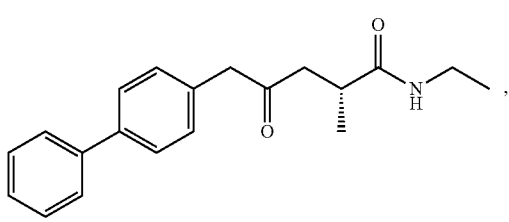

(21) 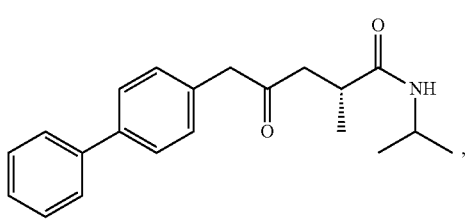

(22) 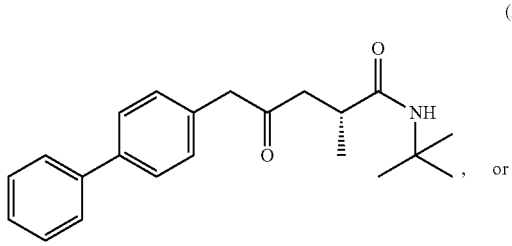

, or

(23) 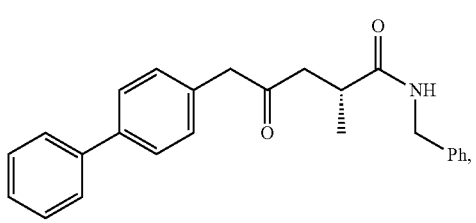

where each Ph is phenyl.

7. The compound of claim 1, wherein $R_2$ is

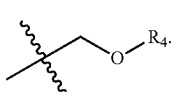

8. The compound of claim 7, wherein $R_1$ is phenyl.
9. The compound of claim 7, wherein $R_4$ is H.
10. The compound of claim 9, wherein $R_1$ is phenyl.

11. A method of preparing a compound of Formula (V):

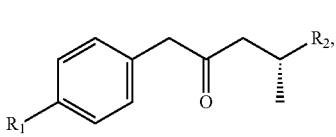 (V)

wherein the compound of Formula (V) is prepared by a deprotection reaction of a compound of Formula (IV):

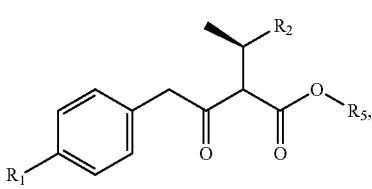 (IV)

in the presence of a base or an acid, wherein:

$R_1$ is phenyl, methoxy, hydroxy, chloro, bromo, iodo, mesylate, triflate or 4-methylbenzenesulfonate;

$R_2$ is

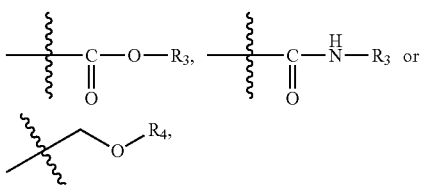

with the proviso that when $R_1$ is phenyl, $R_2$ is not

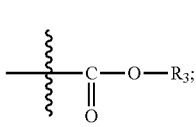

$R_3$ is H, —$(C_1\text{-}C_4)$alkyl or —$(C_1\text{-}C_4)$alkyl-aryl;
$R_4$ is H, —$(C_1\text{-}C_4)$alkyl, —$(C_3\text{-}C_6)$heterocyclyl, —$(C_1\text{-}C_4)$alkyl-aryl, trimethylsilyl, triethylsilyl or t-butyldimethylsilyl; and
$R_5$ is H, —$(C_1\text{-}C_4)$alkyl or —$(C_1\text{-}C_4)$alkyl-aryl.

12. The method of claim 11, the compound of Formula (IV) is prepared by a substitution reaction of a compound of Formula (II) with a compound of Formula (III) in the presence of a base;

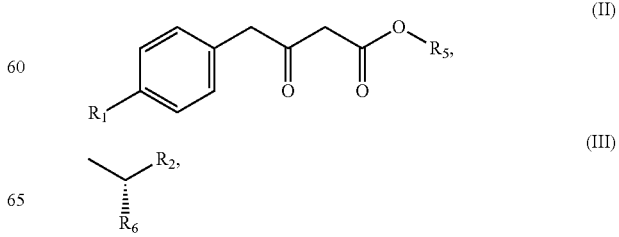

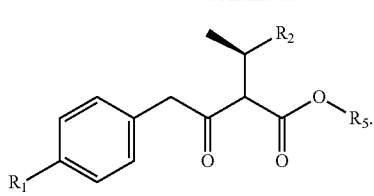
(IV)

13. The method of claim 12, the compound of Formula (II) is prepared by a condensation reaction of a compound of Formula (I);

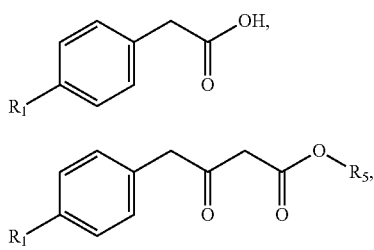

wherein $R_1$ is as defined above; and
$R_5$ is H, —($C_1$-$C_4$)alkyl or —($C_1$-$C_4$)alkyl-aryl.

14. The method according to claim 11, wherein the compound of the Formula (IV) is prepared by a process comprising the following steps:

a) preparing a compound of Formula (II) by a condensation reaction of a compound of Formula (I) in the presence of a base,

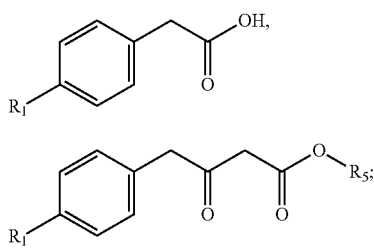

and b) preparing a compound of Formula (IV) by a substitution reaction of the compound of Formula (II) with a compound of Formula (III) in the presence of a strong base;

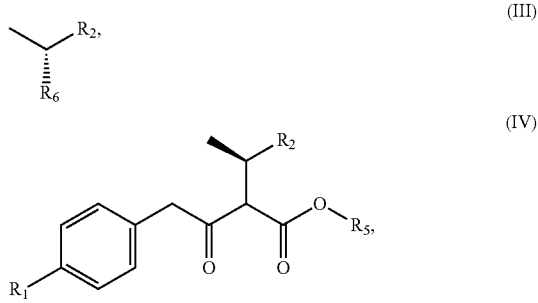

wherein $R_1$ is phenyl;
$R_2$ is

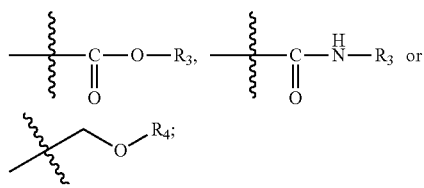

$R_3$ is H, methyl, ethyl, n-propyl, i-propyl, n-butyl, t-butyl or benzyl;
$R_4$ is H, methyl, ethyl, n-propyl, i-propyl, n-butyl, t-butyl, benzyl, trimethylsilyl, triethylsilyl, t-butyldimethylsilyl, triphenylmethyl, or tetrahydrofuryl;
$R_5$ is H, methyl, ethyl, n-propyl, i-propyl, n-butyl or benzyl; and
$R_6$ is triflate, mesylate or 4-methylbenzenesulfonate.

15. The method of claim 14 wherein the compound of Formula (II) is prepared by a condensation reaction of the compound of Formula (I) with N,N'-carbonyldiimidazole and a compound of Formula (VIII):

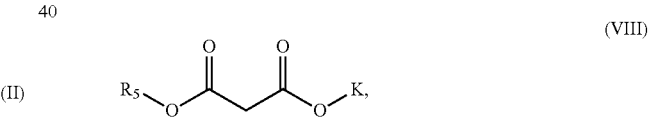

in the presence of magnesium chloride and triethylamine, wherein $R_5$ is H, —($C_1$-$C_4$)alkyl or —($C_1$-$C_4$)alkyl-aryl.

16. The method of claim 14, wherein the compound of Formula (II) is prepared by a condensation reaction of the compound of Formula (I) with Meldrum's acid, 4-dimethylaminopyridine, $R_5$OH and pivaloyl chloride in the presence of N,N-diisopropylethylamine, $R_5$ is H, —($C_1$-$C_4$)alkyl or —($C_1$-$C_4$)alkyl-aryl.

* * * * *